United States Patent
Che et al.

(10) Patent No.: US 10,422,007 B2
(45) Date of Patent: Sep. 24, 2019

(54) MARKERS ASSOCIATED WITH WNT INHIBITORS

(71) Applicants: Jianwei Che, San Diego, CA (US); Jennifer Harris, San Diego, CA (US); Hsin-I Hsieh, San Diego, CA (US); Jie Li, San Diego, CA (US); Jun Liu, San Diego, CA (US); Nicholas Ng, San Diego, CA (US)

(72) Inventors: Jianwei Che, San Diego, CA (US); Jennifer Harris, San Diego, CA (US); Hsin-I Hsieh, San Diego, CA (US); Jie Li, San Diego, CA (US); Jun Liu, San Diego, CA (US); Nicholas Ng, San Diego, CA (US)

(73) Assignee: Novartis AG, Basel (CH)

( * ) Notice: Subject to any disclaimer, the term of this patent is extended or adjusted under 35 U.S.C. 154(b) by 411 days.

(21) Appl. No.: 14/774,212

(22) PCT Filed: Mar. 10, 2014

(86) PCT No.: PCT/IB2014/059585
§ 371 (c)(1),
(2) Date: Sep. 10, 2015

(87) PCT Pub. No.: WO2014/141038
PCT Pub. Date: Sep. 18, 2014

(65) Prior Publication Data
US 2016/0024587 A1 Jan. 28, 2016

Related U.S. Application Data

(60) Provisional application No. 61/776,334, filed on Mar. 11, 2013.

(51) Int. Cl.
*C12Q 1/6886* (2018.01)
*A61K 31/444* (2006.01)
(Continued)

(52) U.S. Cl.
CPC .......... *C12Q 1/6886* (2013.01); *A61K 31/444* (2013.01); *A61K 31/497* (2013.01);
(Continued)

(58) Field of Classification Search
None
See application file for complete search history.

(56) References Cited

U.S. PATENT DOCUMENTS 6,689,744 B2 2/2004 Gao et al.
2011/0237573 A1 9/2011 Cheng et al.

FOREIGN PATENT DOCUMENTS

WO WO2005/049829 A1 6/2005
WO WO2006052128 A1 5/2006
(Continued)

OTHER PUBLICATIONS

Gu, F. et al. Oncology Reports 23;671 (Mar. 1, 2010).*
(Continued)

*Primary Examiner* — Diana B Johannsen
(74) *Attorney, Agent, or Firm* — Michelle Han

(57) ABSTRACT

The invention provides methods of monitoring differential gene expression of biomarkers to determine patient sensitivity to Wnt inhibitor, methods of determining the sensitivity of a cell to an Wnt inhibitor by measuring biomarkers, methods of screening for candidate Wnt inhibitor, Wnt inhibitor for use in head and neck squamous cell carcinoma.

6 Claims, 17 Drawing Sheets

Specification includes a Sequence Listing.

COMPOUND A

COMPOUND B

(51) Int. Cl.
   A61K 31/497   (2006.01)
   A61K 31/501   (2006.01)
   G01N 33/574   (2006.01)
(52) U.S. Cl.
   CPC ..... *A61K 31/501* (2013.01); *G01N 33/57407*
        (2013.01); *G01N 33/57484* (2013.01); *C12Q*
        *2600/106* (2013.01); *C12Q 2600/156*
        (2013.01); *C12Q 2600/158* (2013.01); *G01N*
                                    *2800/52* (2013.01)

(56)            References Cited

FOREIGN PATENT DOCUMENTS

WO     WO2009/074968 A2    6/2009
WO         2010101849 A1    9/2010
WO     WO2011041785 A1    4/2011

OTHER PUBLICATIONS

J. Liu et al: "PD08-11: Targeting Porcupine a Critical Node for Wnt Signalling in Cancer." Cancer Research, vol. 71. No. 24 Supplement, Dec. 15, 2011 (Dec. 15, 2011). pp. PDOB-11, XP055061279, ISSN: 0008-5472, DOI: 10.1158/0008-5472.SABCS11-PD08-11 abstract.
Jamie N. Anastas et al: "WNT signaling pathways as therapeutic targets in cancer", Nature Reviews Cancer, vol. 13 No. 1, Dec. 21, 2012, pp. 11-26. XP055121831. ISSN : 1474-175X, DOI: 10.1038/nrc3419.supplementary table S2.
K. D. Proffitt et al: « Pharmacological Inhibition of the Wnt Acyl transferase PORCN Prevents Growth of WNT-Driven Manmary Cancer, Cancer Research, vol. 73, No. 2, Nov. 27, 2012, pp. 502-507 ISSN: 0008-5472, DOI 10.1158/0008-5472.CAN-12-2258. Abstract.
Shih-Min A. Huang et al: "Tankyrase inhibition stabilizes axin and antagonizes Wnt signaling", Nature, vol. 461, No. 7264, Sep. 16, 2009, pp. 614-620, XP055062115, ISSN: 0028-0836, DOI: 10.1038/nature08356 chapter "XAV939 inhibits growth of DLD-1 cancer cells".
E Clappier et al: "NOTCH1 and FBXW7 mutations have a favorable impact on early response to treatment, but not on outcome, in children with T-cell acute lymphoblastic leukemia (T-ALL) treated on EORTC trials 58881 and 58951", Leukemia, vol. 24, No. 12, Sep. 23, 2010 pp. 2023-2031, XP055122043, ISSN: 0887-6924 , DOI: 10.1038/Ieu.2010.205 chapter "patients and methods".
Kristen R Georgiou et al: "Attenuated Wnt/-catenin signalling mediates methotrexate chemotherapy-induced bone loss and marrow adiposity in rats", Bone, Pergamon Press., Oxford, GB, vol. 50, No. 6, Mar. 22, 2012 (Mar. 22, 2012), pp. 1223-1233, XP028423829, ISSN: 8756-3282, DOI: 10 . 1016/J.Bone .2012.03.027 [retrieved on Mar. 29, 2012] abstract.

Fred E. Bertrand et al: "Developmental pathways in colon cancer: Crosstalk between WNT, BMP, Hedgehog and Notch", Cell Cycle, vol. 11 , No. 23, Dec. 1, 2012 (Dec. 1, 2012), pp. 4344-4351, XP055122055, ISSN: 1538-4101 , DOI : 10.4161jcc.22134 the whole document.
An-Ming Wang et al: "The autonomous notch signal pathway is activated by baicalin and baicalein but is suppressed by niclosamide in K562 cells", Journal of Cellular Biochemistry, vol. 106 , No. 4, Mar. 1, 2009 (Mar. 1, 2009) , pp. 682-692 , XP055122057, ISSN : 0730-2312, DOI: 10.1002jjcb . 22065 the whole document.
Yimin Ma et al: "Inhibition of the Wnt-[beta]-catenin and Notch signaling pathways sensitizes osteosarcoma cells to chemotherapy", Biochemical and Biophysical Research Communications, vol. 431, No. 2, Feb. 1, 2013 (Feb. 1, 2013), pp. 274-279, XP055121072, ISSN : 0006291X, DOI: 10.1016/j.bbrc.2012 . 12 .118.
J. Liu et al: "Targeting Wnt-driven cancer through the inhibition of Porcupine by LGK974", Proceedings of the National Academy of Sciences, vol. 110, No. 50, Nov. 25, 2013 (Nov. 25, 2013), pp. 20224-20229, XP055121007, ISSN: 0027-8424 , DOI: 10.1073/pnas.1314239110.
N. J. Wang et al : "Loss-of-function mutations in Notch receptors in cutaneous and lung squamous cell carcinoma" Proceedings of the National Academy of Sciences, vo 1 . 108, No. 43, Oct. 17, 2011 (Oct. 17, 2011), pp. 17761-17766, XP055122110, ISSN : 0027-8424 , DOI: 10.1073/pnas.1114669108.
S. Fre et al: "Notch and Wnt signals cooperatively control cell proliferation and tumorigenesis in the intestine", Proceedings of the National Academy of Sciences , vol. 106, No. 15, Apr. 14, 2009 (Apr. 14, 2009) , pp. 6309-6314, XP055122117, ISSN: 0027-8424, DOI: 10.1073/pnas .0900427106.
Young Chang Lim et al: "All-trans-retinoic acid inhibits growth of head and neck cancer stem cells by suppression of Wnt/[beta]-catenin pathway", European Journal of Cancer, vol. 48, No. 17, Nov. 1, 2012 (Nov. 1, 2012), pp. 3310-3318, XP055164476, ISSN: 0959-8049, DOI: 10.1016/j.ejca 1206923.
N Agrawal et al: "Exome sequencing of head and neck squamous cell carcinoma reveals inactivating mutations in NOTCH1", Science, vol. 333, No. 6046, Jul. 28, 2011 (Jul. 28, 2011), pp. 1154-1157, XP055164469, ISSN: 0036-8075, DOI: 10.1126/science. 1206923.
Rhee C-S et al: "Wnt and frizzled receptors as potential targets for immunotherapy in head and neck squamous cell carcinomas", Oncogene, Nature Publishing Group, GB, vol. 21, No. 43, Sep. 26, 2002 (Sep. 26, 2002), pp. 6598-6605, XP001191155, ISSN: 0950-9232, DOI: 10.1038/SJ.ONC 1205920.
Database, PubChem. LGK974. Compound Summary for CID 46926973, Jan. 11, 2010, pp. 1-19 retrieved from the Internet: URL: https://pubchem.ncbi.nlm.nih.gov/compound/lgk974#section=Top (accessed Mar. 9, 2018). National Center for Biotechnology information. PubChem Compound Database; CID=46926973.

* cited by examiner

FIGURE 1
1A
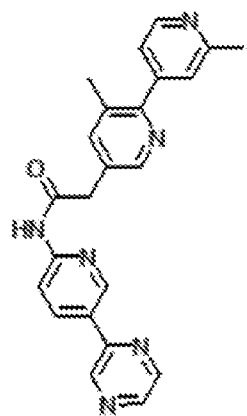
COMPOUND A
1B
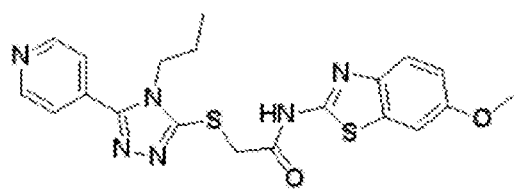
COMPOUND B

Figure 5A

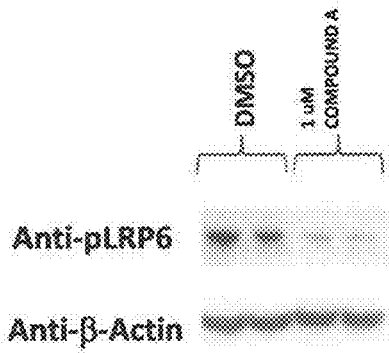

Anti-pLRP6

Anti-β-Actin

Figure 5B

| | | |
|---|---|---|
| WNT10A_H | CHGTXGSCQLKTCW | SEQ ID NO: 2 |
| WNT10B_H | CHGTXGSCQFKTCW | SEQ ID NO: 3 |
| WNT6_HU | CHGLXGSCALRTCW | SEQ ID NO: 4 |
| WNT3_HU | CHGLXGSCEVKTCW | SEQ ID NO: 5 |
| WNT3A_H | CHGLXGSCEVKTCW | SEQ ID NO: 6 |
| WNT1_HU | CHGMXGSCTVKTCW | SEQ ID NO: 7 |
| WNT4_HU | CHGVXGSCEVKTCW | SEQ ID NO: 8 |
| WNT7A_H | CHGVXGSCTTKTCW | SEQ ID NO: 9 |
| WNT7B_H | CHGVXGSCTTKTCW | SEQ ID NO: 10 |
| WNT16_H | CHGVXGSCAVKTCW | SEQ ID NO: 11 |
| WNT2_HU | CHGVXGSCTLRTCW | SEQ ID NO: 12 |
| WNT2B_H | CHGVXGSCTLRTCW | SEQ ID NO: 13 |
| WNT5A_H | CHGVXGSCSLKTCW | SEQ ID NO: 14 |
| WNT5B_H | CHGVXGSCSLKTCW | SEQ ID NO: 15 |
| WNT8A_H | CHGIXGSCSIQTCW | SEQ ID NO: 16 |
| WNT8B_H | CHGVXGSCTTQTCW | SEQ ID NO: 17 |
| WNT11_H | CHGVXGSCSIRTCW | SEQ ID NO: 18 |
| WNT9A_H | CHGVXGSCTVRTCW | SEQ ID NO: 19 |
| WNT9B_H | CHGVXGSCAVRTCW | SEQ ID NO: 20 |

Figure 5C

| Assay | COMPOUND A IC$_{50}$ (nM) |
|---|---|
| Wnt1 (RGA) | 1.1 |
| Wnt2 (RGA) | 0.2 |
| Wnt3 (RGA) | 0.6 |
| Wnt3a (RGA) | 0.9 |
| Wnt6 (RGA) | 0.2 |
| Wnt7a (RGA) | 2.4 |
| Wnt9a (RGA) | 0.05 |

FIGURE 7

| No | Head neck cancer cell line names | Axin2 reduction response | Axin2 inhibition (1-treated/control) | No | Head neck cancer cell line names | Axin2 reduction response | Axin2 inhibition (1-treated/control) |
|---|---|---|---|---|---|---|---|
| 1 | A-253 | No | 0 | 21 | UMSCC 10A | Yes | 0.5 |
| 2 | CAL27 | Yes | 0.7 | 22 | UMSCC 10B | No | 0.3 |
| 3 | Detroit 562 | No | 0.2 | 23 | UMSCC 11A | Yes | 0.6 |
| 4 | FaDu | No | 0 | 24 | UMSCC 11B | Yes | 0.6 |
| 5 | HN30 | Yes | 0.9 | 25 | UMSCC 12 | No | 0.4 |
| 6 | Hs 840.T | No | 0 | 26 | UMSCC 13 | Yes | 0.9 |
| 7 | SCC-4 | No | 0.4 | 27 | UMSCC 14A | No | 0.0 |
| 8 | SCC-9 | No | 0 | 28 | UMSCC 14B | Yes | 0.5 |
| 9 | SCC-25 | No | 0.1 | 29 | UMSCC 14C | Yes | 0.7 |
| 10 | SNU-1066 | No | 0.3 | 30 | UMSCC 16 | No | 0.3 |
| 11 | SNU-1076 | Yes | 0.9 | 31 | UMSCC 17A | No | 0.3 |
| 12 | UMSCC 1 | Yes | 0.9 | 32 | UMSCC 17B | Yes | 0.6 |
| 13 | UMSCC 2 | No | 0.2 | 33 | UMSCC 19 | Yes | 0.5 |
| 14 | UMSCC 3 | No | 0.0 | 34 | UMSCC 21A | No | 0.1 |
| 15 | UMSCC 4 | No | 0.3 | 35 | UMSCC 22A | No | 0.3 |
| 16 | UMSCC 5 | No | 0.3 | 36 | UMSCC 22B | No | 0.0 |
| 17 | UMSCC 6 | Yes | 0.9 | 37 | UMSCC 23 | No | 0.3 |
| 18 | UMSCC 7 | No | 0.4 | 38 | UMSCC 25 | Yes | 0.9 |
| 19 | UMSCC 8 | No | 0.4 | 39 | UMSCC 26 | No | 0.3 |
| 20 | UMSCC 9 | Yes | 0.8 | 40 | UMSCC 28 | Yes | 0.7 |

FIGURE 7 – cont.

| No | Head neck cancer cell line names | Axin2 reduction response | Axin2 inhibition (1-treated/control) | No | Head neck cancer cell line names | Axin2 reduction response | Axin2 inhibition (1-treated/control) |
|---|---|---|---|---|---|---|---|
| 41 | UMSCC 29 | Yes | 0.7 | 63 | UMSCC 53 | No | 0.1 |
| 42 | UMSCC 30 | No | 0.3 | 64 | UMSCC 55 | No | 0.0 |
| 43 | UMSCC 31 | No | 0 | 65 | UMSCC 58 | No | 0.4 |
| 44 | UMSCC 33 | No | 0.2 | 66 | UMSCC 59 | Yes | 0.7 |
| 45 | UMSCC 34 | Yes | 0.9 | 67 | UMSCC 60 | No | 0.2 |
| 46 | UMSCC 35 | Yes | 0.6 | 68 | UMSCC 62 | No | 0.3 |
| 47 | UMSCC 36 | No | 0.0 | 69 | UMSCC 63 | Yes | 0.8 |
| 48 | UMSCC 37 | No | 0.0 | 70 | UMSCC 67 | No | 0.2 |
| 49 | UMSCC 38 | Yes | 0.5 | 71 | UMSCC 69 | No | 0.4 |
| 50 | UMSCC 39 | No | 0.0 | 72 | UMSCC 70 | No | 0.3 |
| 51 | UMSCC 40 | No | 0.3 | 73 | UMSCC 71 | No | 0.2 |
| 52 | UMSCC 41 | Yes | 0.6 | 74 | UMSCC 73B | No | 0.4 |
| 53 | UMSCC 42 | No | 0.3 | 75 | UMSCC 74A | No | 0.0 |
| 54 | UMSCC 43 | Yes | 0.7 | 76 | UMSCC 74B | No | 0.0 |
| 55 | UMSCC 44 | No | 0.0 | 77 | UMSCC 76 | Yes | 0.7 |
| 56 | UMSCC 45 | Yes | 0.5 | 78 | UMSCC 77 | No | 0.2 |
| 57 | UMSCC 46 | Yes | 0.5 | 79 | UMSCC 78 | No | 0.0 |
| 58 | UMSCC 47 | No | 0.3 | 80 | UMSCC 80 | No | 0.0 |
| 59 | UMSCC 49 | No | 0.2 | 81 | UMSCC 81A | No | 0.0 |
| 60 | UMSCC 50 | No | 0.1 | 82 | UMSCC 81B | No | 0.3 |
| 61 | UMSCC 51 | No | 0.4 | 83 | UMSCC 83A | No | 0.2 |
| 62 | UMSCC 52 | No | 0.2 | 84 | UMSCC 83B | No | 0.4 |

FIGURE 7 – cont.

| No | Head neck cancer cell line names | Axin2 reduction response | Axin2 inhibition (1-treated/control) | No | Head neck cancer cell line names | Axin2 reduction response | Axin2 inhibition (1-treated/control) |
|---|---|---|---|---|---|---|---|
| 85 | UMSCC 85 | No | 0.0 | 91 | UMSCC 98 | No | 0.1 |
| 86 | UMSCC 90 | Yes | 0.5 | 92 | UMSCC 103 | No | 0.0 |
| 87 | UMSCC 92 | Yes | 0.9 | 93 | UMSCC 104 | No | 0.0 |
| 88 | UMSCC 93 | Yes | 0.6 | 94 | UMSCC 105 | No | 0.3 |
| 89 | UMSCC 94 | No | 0.3 | 95 | UMSCV 1A | No | 0.0 |
| 90 | UMSCC 97 | Yes | 0.8 | 96 | UMSCV 6 | No | 0.1 |

FIGURE 8
8A
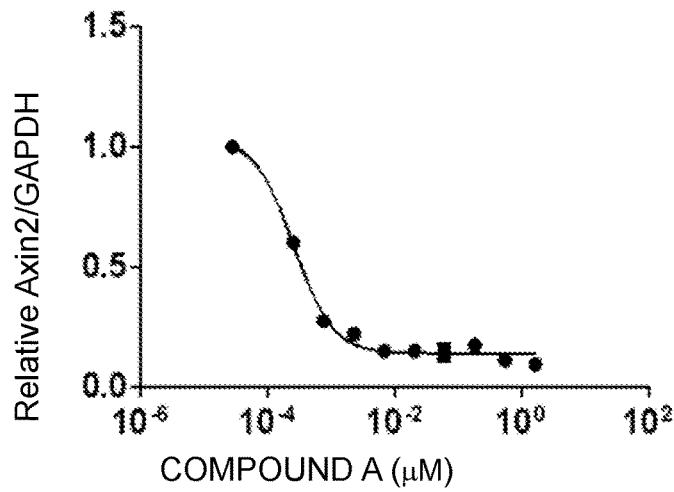
8B
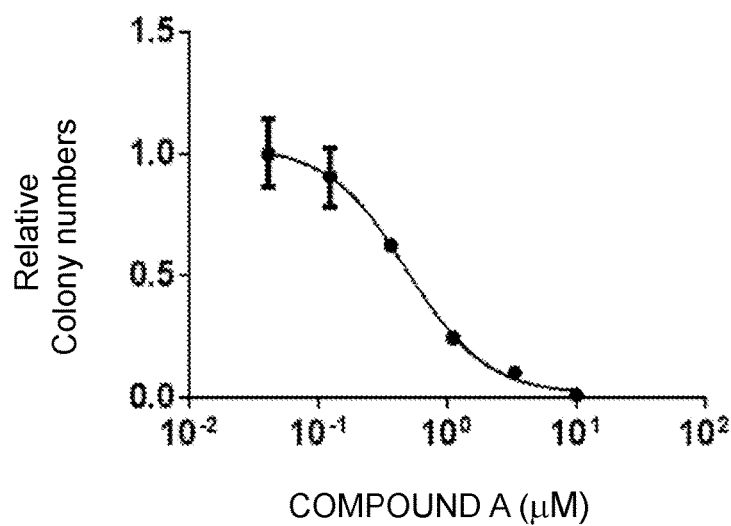

FIGURE 9
9A
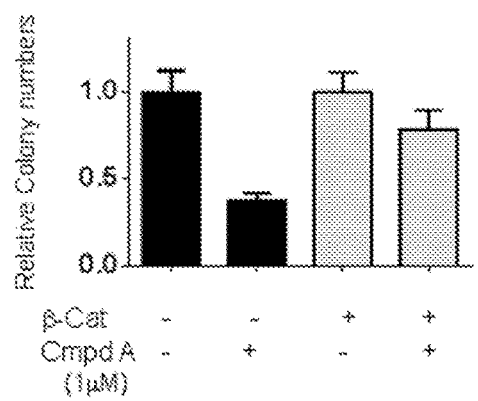
9B
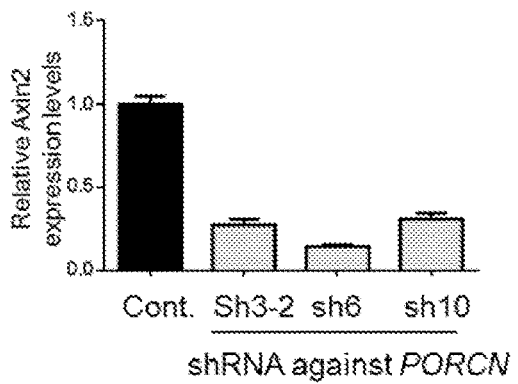
9C
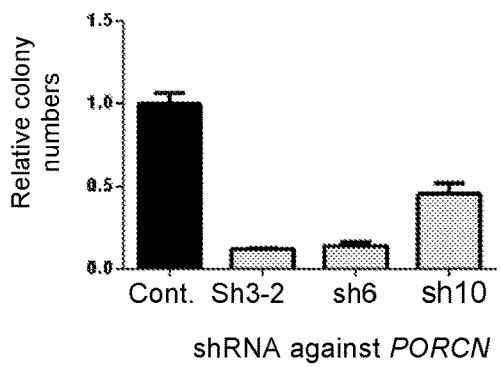

FIGURE 10
10A
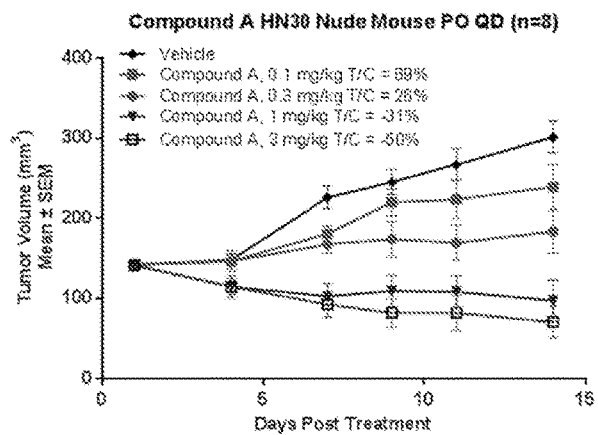
10B
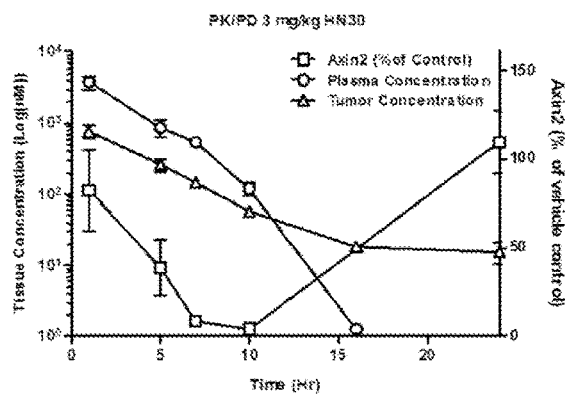
10C
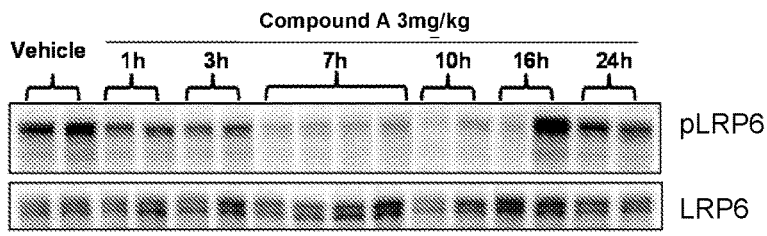

FIGURE 11

| Genes | Mutation Occurrence |
|---|---|
| TP53 | 27/40 (68%) |
| CDKN2A | 7/40 (18%) |
| Notch1 | 10/40 (25%) |
| PTEN | 1/40 (3%) |
| HRAS | 5/40 (13%) |
| PIK3CA | 5/40 (13%) |
| Notch2 | 5/40 (13%) |
| Notch3 | 2/40 (5%) |

FIGURE 12

| Gene | Genomic Change | Amino Acid change | Responsive Mutants | Resistant Mutants | Enrichment Factor |
|---|---|---|---|---|---|
| FAM58A | g.chrX:152864477G>GC\|g.chrX:152858079GC>G\|g.chrX:152864513G>GC | A18fs, A181fs, A6fs | 11 | 1 | 6.6 |
| FLJ43860 | g.chr8:142459777C>CA | L850fs | 7 | 1 | 4.2 |
| NOTCH1 | g.chr9:139411813AC>A\|g.chr9:139411793TG>T\|g.chr9:139410488C>CT\|g.chr9:139417470C>A\|g.chr9:139412259CTGGCACGG>C\|g.chr9:139417398C>A | E488fs, G192X, E216X, K538fs, A495fs, P460fs, | 5 | 1 | 3.0 |
| OR7G3 | g.chr19:9236916AG>A | A237fs | 8 | 2 | 2.4 |
| CCDC168 | g.chr13:103386417C>A\|g.chr13:103384147C>T | E5544X, W6300X | 4 | 1 | 2.4 |
| ZNF527 | g.chr19:37879852C>CTGTG\|g.chr19:37879854AT>A | P301fs, Y302fs | 7 | 2 | 2.1 |
| CDKN2A | g.chr9:21971123TGA>T\|g.chr9:21968242C>T\|g.chr9:21971186G>A\|g.chr9:21971028C>T\|g.chr9:21971120G>A | S78fs, W110X, R58X, R80X | 4 | 0 | NA | fs: frameshift; X: nonsense mutations

FIGURE 13
13A
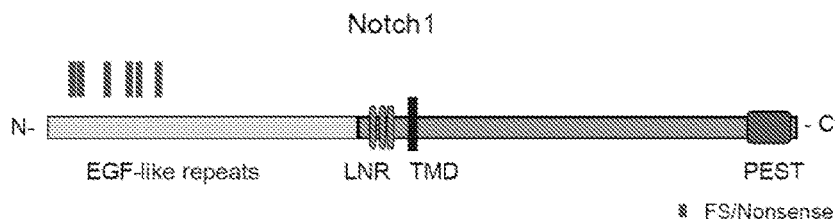
13B
| Cell Line | Responsive to COMPOUND A | Notch1 mutation |
|---|---|---|
| UMSCC 25 | Yes | E488fs |
| UMSCC 28 | Yes | A495fs |
| UMSCC 29 | Yes | K538fs |
| UMSCC 47 | No | G192X |
| UMSCC 59 | Yes | P460fs |
| UMSCC 76 | Yes | E216X |
13C
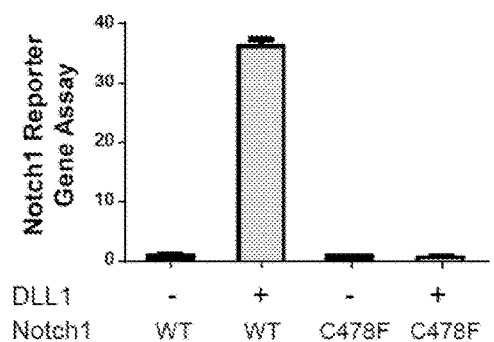

FIGURE 14
14A
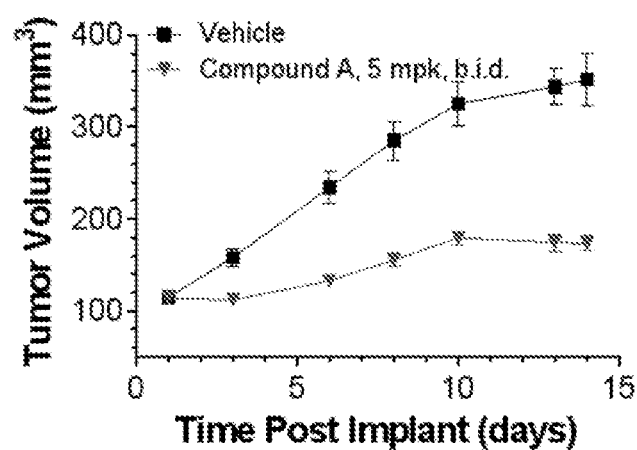
14B
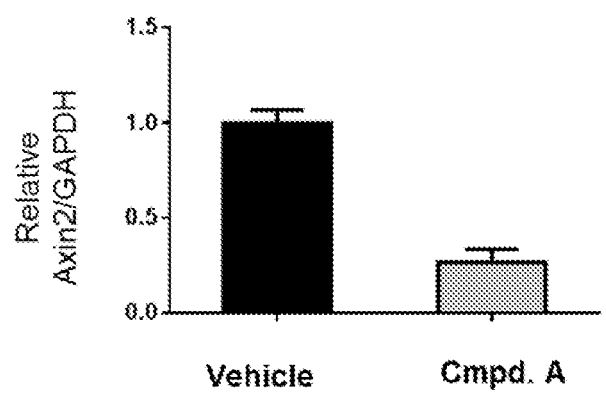

Figure 15

| Cell Line | Responsive to COMPOUND A | FAT1 mutation |
|---|---|---|
| UMSCC 63 | Yes | P2559S |
| UMSCC 11A | Yes | D4109G |
| UMSCC 41 | Yes | G4147C |
| UMSCC 35 | Yes | P2559L |
| UMSCC-25 | Yes | N524fs |
| UMSCC-43 | Yes | M1150fs |
| UMSCC 8 | No | Q3887X |

Figure 16

| Cell Line | Responsive to COMPOUND A | HRAS mutation |
|---|---|---|
| UMSCC 17B | Yes | Q61L |
| UMSCC 43 | Yes | G12V |
| UMSCC 63 | Yes | G13D |
| UMSCC 17A | No | Q61L |
| HN30 | Yes | G12D |

SEQUENCE LISTING

<160> NUMBER OF SEQ ID NOS: 20

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Gly Ser Cys
1

<210> SEQ ID NO 2
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 2

Cys His Gly Thr Ser Gly Ser Cys Gln Leu Lys Thr Cys Trp
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys His Gly Thr Ser Gly Ser Cys Gln Phe Lys Thr Cys Trp
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys His Gly Leu Ser Gly Ser Cys Ala Leu Arg Thr Cys Trp
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys His Gly Leu Ser Gly Ser Cys Glu Val Lys Thr Cys Trp
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys His Gly Leu Ser Gly Ser Cys Glu Val Lys Thr Cys Trp
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys His Gly Met Ser Gly Ser Cys Thr Val Arg Thr Cys Trp
1               5                   10
```

```
<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys His Gly Val Ser Gly Ser Cys Glu Val Lys Thr Cys Trp
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys His Gly Val Ser Gly Ser Cys Thr Thr Lys Thr Cys Trp
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys His Gly Val Ser Gly Ser Cys Thr Thr Lys Thr Cys Trp
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys His Gly Val Ser Gly Ser Cys Ala Val Lys Thr Cys Trp
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys His Gly Val Ser Gly Ser Cys Thr Leu Arg Thr Cys Trp
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 13

Cys His Gly Val Ser Gly Ser Cys Thr Leu Arg Thr Cys Trp
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys His Gly Val Ser Gly Ser Cys Ser Leu Lys Thr Cys Trp
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys His Gly Val Ser Gly Ser Cys Ser Leu Lys Thr Cys Trp
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys His Gly Ile Ser Gly Ser Cys Ser Ile Gln Thr Cys Trp
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys His Gly Val Ser Gly Ser Cys Thr Thr Gln Thr Cys Trp
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys His Gly Val Ser Gly Ser Cys Ser Ile Arg Thr Cys Trp
1               5                   10

<210> SEQ ID NO 19
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 19

Cys His Gly Val Ser Gly Ser Cys Thr Val Arg Thr Cys Trp
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys His Gly Val Ser Gly Ser Cys Ala Val Arg Thr Cys Trp
1               5                   10
```

MARKERS ASSOCIATED WITH WNT INHIBITORS

SEQUENCE LISTING

The instant application contains a Sequence Listing which has been submitted electronically in ASCII format and is hereby incorporated by reference in its entirety. Said ASCII copy, created on Mar. 22, 2018 is named PAT055634-US-PCT_SL.txt and is 5,652 bytes in size.

FIELD OF THE INVENTION

The present invention relates to the field of pharmacogenomics, and the use of biomarkers useful in determining patient sensitivity prior to treatment, following patient response after treatment, cancer sensitivity, screening of compounds, methods of treatment and pharmaceutical composition for use in the treatment.

BACKGROUND

Wnt signaling is one of the key oncogenic pathways in multiple cancers[1,2]. Upon binding to its receptors, low density lipoprotein receptor-related protein 5/6 (LRP5/6) and Frizzled (FZD) (both are single pass transmembrane receptors required for Wnt signalling) at the plasma membrane, Wnt ligand triggers the disruption of β-catenin degradation machinery composing of Axin2, GSK3β, APC and other proteins, which leads to the accumulation of β-catenin in the cytoplasm[3]. Elevated levels of β-catenin ultimately leads to its translocation into the nucleus to form a complex with LEF/TCF, and drive downstream gene expression[3].

Dysregulation of Wnt signaling[1] can occur through mutations of downstream components such as APC and β-catenin that are well documented in colon cancer[1]. In addition, overexpression of Wnt ligands or co-stimulants, such as RSPO2/3, or silencing of Wnt inhibitor genes have been reported in various cancers[1,4]. Furthermore, mutations of pan-Wnt pathway components, such as Axin1/2 or RSPO co-receptors RNF43/ZNFR3, play a potential key role in pancreatic, colon, and hepatocellular carcinoma[4-6]. Both unbiased and targeted mutations of the Wnt pathway in animal models have demonstrated the oncogenic signaling function of this pathway[7,8]. In addition to the canonical Wnt pathway, there is emerging evidence that non-canonical Wnt signaling, through FZD and VANGL, is critical for various aspects of tumorigenesis including cell migration and tumor metastasis[9].

Both canonical and non-canonical Wnt signaling activities are dependent on the Wnt ligand. During the biosynthesis of Wnt ligands, Wnt undergoes post-translational acylation that is mediated by Porcupine (PORCN), a membrane bound O-acyltransferase[3,10]. PORCN is specific and dedicated to Wnt post-translational acylation, which is required for subsequent Wnt secretion[11]. Loss of PORCN leads to inhibition of the Wnt ligand driven signaling activities in knockout mouse models[12,13]. In humans, loss of function (LoF) mutation of the PORCN gene causes focal dermal hypoplasia in an X-linked dominant disorder associated with a variety of congenital abnormalities in both heterozygotes and those with mosaicism for the PORCN gene. This phenotype is consistent with the role of Wnt signaling pathway during embryogenesis and development[14,15].

Success so far in therapeutically targeting the Wnt signalling has been limited. This is largely due to the lack of effective therapeutic agents for targets in the Wnt pathway and the lack of a defined patient population that would be sensitive to a Wnt inhibitor. As a result to differences in a complex cascade of regulatory mechanisms in the cell cycle and differential gene expression different cancer types may respond differently to the same active compound. Knowledge on specific biomarkers which indicate the sensitivity of cells to the therapy with a PORCN inhibitor or Wnt inhibitor is also scarce.

SUMMARY OF THE INVENTION

The invention relates to the analysis that Notch1, Notch2, Notch3, AXIN2, LEF1, NKD1, SFRP2, FRZB, SFRP4, DKK2, FAM58A, FLJ43860, CDKN2A, CCDC168, ZNF527, HRAS, FAT1, OR7G3, WNT11, WNT10A, WNT3, WNT7A, and/or DTX3L act as specific biomarkers in determining the sensitivity of cells to Wnt inhibitors. The invention relates to the analysis that at least one of the biomarkers selected from Table 1 provides a "gene signature" for a Wnt inhibitor that has increased accuracy and specificity in predicting which cancer cells or cancers are sensitive to a Wnt inhibitor. The method analyzes the expression, gene expression, mutation status, protein level or a function of at least one of the biomarkers selected from Table 1 in a cancer sample taken from a patient and compared to a control predicts the sensitivity of the cancer sample to an Wnt inhibitor. The pattern of expression level changes may be indicative of a favorable response or an unfavorable one. In addition, the gene signature selected from the Table 1 has increased predictive value because it also indicates that the Wnt pathway is functional. The disclosure provides also an example of "personalized medicine" wherein patients are treated based on a functional genomic signature that is specific to that individual.

The predictive value of at least one biomarker disclosed herein can also be used after treatment with a Wnt inhibitor to determine if the patient remains sensitive to the treatment. Once the Wnt inhibitor has been administered, the biomarkers are used to monitor the continued sensitivity of the patient to the treatment with a Wnt inhibitor. The disclosure also relates to the up or down regulation of the expression of the identified genes before and after the treatment with a Wnt inhibitor. This is useful in determining that patients receive the correct course of treatment. The invention comprises a method of predicting and monitoring the sensitivity of a patient to the treatment with a Wnt inhibitor. The method includes the step of administration of a Wnt inhibitor to the patient and measurement of biomarker gene expression on a biological sample obtained from the patient. The response of the patient is evaluated based on the detection of gene expression of at least one biomarker selected from the Table 1. Detection and/or alteration in the level of expression of at least one biomarker compared to a control is indicative of the sensitivity of the patient to the treatment. The pattern of expression level changes can be indicative of a favorable patient response or an unfavorable one.

The disclosure also provides Wnt inhibitors for use in the treatment of head and neck cancer. Particularly good therapeutic response is predicted in the patients that have in their cancer sample differentially downregulated expression of at least one biomarker selected from Table 1 compared to a control.

The aspects, features and embodiments of the present disclosure are summarized in the following items and can be used respectively alone or in combination:

1. A method of predicting the sensitivity of a cancer patient for treatment with a Wnt inhibitor, the method comprising:
a) providing a cancer sample from a cancer patient
b) measuring differential gene expression of at least one biomarker selected from Table 1, in the cancer sample obtained from the patient; and
c) comparing the differential gene expression of the at least one biomarker with gene expression of said biomarker in a control sample,
d) correlating the increase or decrease in gene expression comparison with the patient sensitivity to the treatment with the Wnt inhibitor.

2. A method of treating a cancer patient with a Wnt inhibitor comprising:
a) providing a cancer sample from a cancer patient
b) measuring differential gene expression of at least one biomarker selected from Table 1, in the cancer sample obtained from the patient;
c) comparing the differential gene expression of the at least one biomarker with gene expression of the biomarker in a control sample;
d) determining sensitivity of the patient to the Wnt inhibitor; and
e) administering an effective amount of the Wnt inhibitor to a patient who has been determined to be sensitive to the Wnt inhibitor.

3. A method of predicting the sensitivity of a cancer cell to a Wnt inhibitor, the method comprising: a) measuring differential gene expression of at least one biomarker selected from Table 1 in the cell; b) comparing the differential gene expression of the at least one biomarker selected from Table 1 with gene expression from a normal or control cell;
c) predicting the sensitivity of the cancer cell to the Wnt inhibitor from the comparison of the differential gene expression.

4. A method of determining the sensitivity of a cancer cell to a Wnt inhibitor, the method comprising:
a) contacting a cancer cell with at least one Wnt inhibitor;
b) measuring differential gene expression of at least one biomarker selected from Table 1 in the cell contacted with the Wnt inhibitor;
c) comparing the differential gene expression of the at least one biomarker with gene expression of the biomarker from an untreated or placebo treated control cell;
d) correlating the increase or decrease in the expression of at the least one biomarker when compared with the expression of the at least one biomarker from the untreated or placebo treated control cell to the sensitivity of the cancer cell to a Wnt inhibitor.

5. The method of any one of items 1 to 4, wherein more than one biomarker is selected from Table 1.

6. The method of any one of items 1 to 5, wherein the biomarker is Notch1.

7. The method of item 6, wherein the Notch1 has mutation in the extracellular domain.

8. The method of any one of items 1 to 7, wherein comparing the differential gene expression of the at least one biomarker with gene expression of a control sample indicates a functional Wnt pathway.

9. The method of any one of items 1 to 8, wherein the cancer is a head and neck squamous cell carcinoma.

10. The method of item 2 or 4, wherein the cancer is treated with a Wnt inhibitor and shows differential expression of Axin2, LEF1 and/or NKD1 compared to the expression in a cancer sample that is sensitive to a Wnt inhibitor.

11. The method of any one of items 1 to 10, wherein the IC50 of the cancer cell contacted with at least one Wnt inhibitor is less than 1 μM, preferably less than 0.5 μM, more preferably less than 0.2 μM.

12. The method of item 11, wherein the cell is contacted by the Wnt inhibitor at least at two different time points.

13. The method of any one of items 4, 11 or 12, wherein the cell is contacted by two different Wnt inhibitors at step a) simultaneously or sequentially.

14. The method of any one of items 4, or 11 to 13, wherein the steps b) and c) are repeated at a time points selected from the group consisting of: 4 hours, 8 hours, 16 hours, 24 hours, 48 hours, 3 days, 1 week, 1 month and several months after administration of each dose of the Wnt inhibitor.

15. A Wnt inhibitor for use in the treatment of a cancer in a patient, wherein the patient is selected on the basis of:
a) measuring differential gene expression of at least one biomarker selected from Table 1, in a cancer sample obtained from the patient;
b) comparing the differential gene expression of the at least one biomarker with gene expression of the biomarker in a control sample;
c) determining sensitivity of the patient to the Wnt inhibitor; and
d) selecting the patient that is sensitive to the Wnt inhibitor.

16. A Wnt inhibitor for use in the treatment of cancer in a patient having differential gene expression of at least one biomarker selected from Table 1 as compared to a control gene expression, wherein the differential gene expression correlates with the patient being sensitive to the Wnt inhibitor.

17. The Wnt inhibitor for use in the treatment of cancer according to items 15 or 16, wherein more than one biomarker is selected from Table 1.

18. The Wnt inhibitor for use in the treatment of cancer according to any one of items 15 to 17, wherein the biomarker is Notch1.

19. The Wnt inhibitor for use in the treatment of cancer according to any one of items 15 to 18, wherein the Notch1 has mutation in extracellular domain.

20. The Wnt inhibitor for use in the treatment of cancer according to any one of items 15 to 19, wherein cancer is a head and neck squamous cell carcinoma, preferably the cancer sample after treatment with a Wnt inhibitor is showing Axin2, LEF1 and/or NKD1 expression of a cancer sample that is sensitive to a Wnt inhibitor.

21. A pharmaceutical composition comprising a Wnt inhibitor for use in the treatment of cancer in a patient, wherein the patient is selected on the basis of showing a gene expression of at least one biomarker selected from Table 1 in a cancer cell sample obtained from said patient compared to a normal control cell sample, wherein the differential gene expression correlates with the patient being sensitive to the Wnt inhibitor.

22. A pharmaceutical composition comprising a Wnt inhibitor for use in the treatment of cancer in a patient showing differential gene expression of at least one biomarker selected from Table 1 as compared to a control gene expression, wherein the differential gene expression correlates with the patient being sensitive to the Wnt inhibitor.

23. The pharmaceutical composition comprising a Wnt inhibitor for use in the treatment of cancer according to items 21 or 22, wherein more than one biomarker is selected from Table 1.

24. The pharmaceutical composition comprising a Wnt inhibitor for use in the treatment of cancer according to any one of items 21 to 23, wherein the biomarker is Notch1.

25. The pharmaceutical composition comprising a Wnt inhibitor for use in the treatment of cancer according to any one of items 21 to 24, wherein the Notch1 has mutation in extracellular domain.

26. The pharmaceutical composition comprising a Wnt inhibitor for use in the treatment of cancer according to any one of items 21 to 25, wherein cancer is a head and neck squamous cell carcinoma.

27. A kit for predicting the sensitivity of a cancer patient for treatment with a Wnt inhibitor comprising
i) means for detecting the expression of the biomarkers selected from Table 1; and
ii) instructions how to use said kit.

28. Use of the kit according to item 27 for any of the methods of items 1 to 14.

29. A Wnt inhibitor for use in the treatment of head and neck squamous cell carcinoma.

30. A Wnt inhibitor for use in the treatment of head and neck squamous cell carcinoma according to item 29, wherein the Wnt inhibitor is administered to a patient with a cancer showing differential gene expression of at least one biomarker selected from Table 1 compared to a control gene expression, wherein the differential gene expression correlates with the patient being sensitive to the Wnt inhibitor.

31. The Wnt inhibitor for use in the treatment of head and neck squamous cell carcinoma according to item 30, wherein the biomarker is Notch1.

32. The method of any one of items 1 to 14, the Wnt inhibitor for use in the treatment of cancer according to any one of items 15 to 20, the pharmaceutical composition according to any one of items 21 to 26, or a Wnt inhibitor for use in the treatment of head and neck squamous cell carcinoma according to item 29, wherein the Wnt inhibitor is administered in a therapeutically effective amount.

33. The Wnt inhibitor for use in the treatment of a cancer in a patient according to any one of items 15 to 20, wherein a therapeutically effective amount of the Wnt inhibitor is administered to the patient.

34. The Wnt inhibitor for use in the treatment of a cancer in a patient according to items 33, wherein the therapeutically effective amount of the Wnt inhibitor is selectively administered to the patient that is determined sensitive to the Wnt inhibitor, or selectively administering a therapeutically effective amount of a drug other than the Wnt inhibitor to the patient on the basis of the patient not being sensitive to the Wnt inhibitor.

35. The method of any one of items 1 to 14, the Wnt inhibitor for use in the treatment of cancer according to any one of items 15 to 20, 33 or 34, the pharmaceutical composition according to any one of items 21 to 26, the kit according to item 27 or a Wnt inhibitor for use in the treatment of head and neck squamous cell carcinoma according to any one of items 29 to 32, wherein the Wnt inhibitor is a compound of Formula (1):

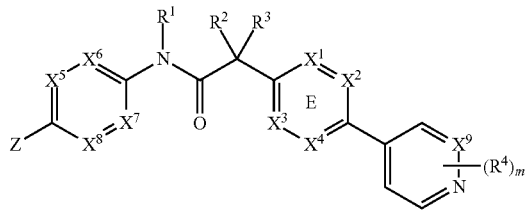

(1)

or a physiologically acceptable salt thereof, wherein:
wherein $X^1$, $X^2$, $X^3$ and $X^4$ is selected from N and $CR^7$;
one of $X^5$, $X^6$, $X^7$ and $X^8$ is N and the others are CH;
$X^9$ is selected from N and CH;
Z is selected from phenyl, pyrazinyl, pyridinyl, pyridazinyl and piperazinyl; wherein each phenyl, pyrazinyl, pyridinyl, pyridazinyl or piperazinyl of Z is optionally substituted with an $R^6$ group;

$R^1$, $R^2$ and $R^3$ are hydrogen;
m is 1;
$R^4$ is selected from hydrogen, halo, difluoromethyl, trifluoromethyl and methyl;
$R^6$ is selected from hydrogen, halo and $-C(O)R^{10}$; wherein $R^{10}$ is methyl; and
$R^7$ is selected from hydrogen, halo, cyano, methyl and trifluoromethyl.

36. The method of any one of items 1 to 14, the Wnt inhibitor for use in the treatment of cancer according to any one of items 15 to 20, 33 or 34, the pharmaceutical composition according to any one of items 21 to 26, the kit according to item 27, or a Wnt inhibitor for use in the treatment of head and neck squamous cell carcinoma according to any one of items 29 to 32, wherein the Wnt inhibitor is a compound selected from the group of N-[5-(3-fluorophenyl)pyridin-2-yl]-2-[5-methyl-6-(pyridazin-4-yl)pyridin-3-yl]acetamide; 2-[5-methyl-6-(2-methylpyridin-4-yl)pyridin-3-yl]-N-[5-(pyrazin-2-yl)pyridin-2-yl]acetamide; N-(2,3'-bipyridin-6'-yl)-2-(2',3-dimethyl-2,4'-bipyridin-5-yl)acetamide; N-(5-(4-acetylpiperazin-1-yl)pyridin-2-yl)-2-(2'-methyl-3-(trifluoromethyl)-2,4'-bipyridin-5-yl)acetamide; N-(5-(4-acetylpiperazin-1-yl)pyridin-2-yl)-2-(2'-fluoro-3-methyl-2,4'-bipyridin-5-yl)acetamide; and 2-(2'-fluoro-3-methyl-2,4'-bipyridin-5-yl)-N-(5-(pyrazin-2-yl)pyridin-2-yl)acetamide; or a pharmaceutically acceptable salt thereof.

37. The method of any one of items 1 to 14, the Wnt inhibitor for use in the treatment of cancer according to any one of items 15 to 20, 33 or 34, the pharmaceutical composition according to any one of items 21 to 26, the kit according to item 27, or a Wnt inhibitor for use in the treatment of head and neck squamous cell carcinoma according to any one of items 29 to 32, wherein the Wnt inhibitor is 2-[5-methyl-6-(2-methylpyridin-4-yl)pyridin-3-yl]-N-[5-(pyrazin-2-yl)pyridin-2-yl]acetamide.

38. Any one of items 1 to 37, wherein expression or gene expression is DNA expression, DNA copy number, mRNA expression, cDNA expression, protein transcription, protein expression, DNA modification, cDNA modification, mRNA modification, protein modification, DNA function, cDNA function, mRNA function, protein function, DNA mutation, cDNA mutation, mRNA mutation, protein mutation, or combinations thereof; preferably is DNA mutation.

39. Any one of items 1 to 38, wherein the biomarker is selected from the group of Notch1, Notch2, Notch3, AXIN2, LEF1, NKD1, SFRP2, FRZB, SFRP4, DKK2, FAM58A, FLJ43860, CDKN2A, OR7G3, WNT11, WNT10A, WNT3, WNT7A and DTX3L.

40. Any one of items 1 to 38, wherein the biomarker is selected from the group of Notch1, Notch2, Notch3, AXIN2, LEF1, NKD1, SFRP2, FRZB, SFRP4, DKK2, FAM58A, FLJ43860, CDKN2A, CCDC168, ZNF527, HRAS, FAT1, OR7G3, WNT11, WNT10A, WNT3, WNT7A and DTX3L.

41. Any one of items 1 to 38, wherein the biomarker is selected from the group of Notch1, Notch2, Notch3, SFRP2, FRZB, SFRP4 and DKK2.

42. Any one of items 1 to 38, wherein the biomarker is selected from the group of Notch1, Notch2 and Notch3.

43. Any one of items 1 to 38, wherein the biomarker is Notch1.

44. Any one of items 1 to 38, wherein the biomarker is selected from the group of Notch1, Notch2, Notch3, SFRP2, FRZB, SFRP4, DKK2, FAM58A, FLJ43860, CDKN2A, CCDC168, ZNF527, HRAS, FAT1, OR7G3, WNT11, WNT10A, WNT3 and WNT7A.

45. Any one of items 1 to 38, wherein the biomarker is HRAS or FAT1.
46. Any one of items 1 to 38, wherein the biomarker is selected from the group consisting of FAM58A, FLJ43860, NOTCH1, OR7G3, CCDC168, ZNF527 and CDKN2A.
47. The embodiment of any one of items 1 to 38, wherein the biomarker is selected from the group of Notch1, Notch2, Notch3, FAM58A, FLJ43860, CDKN2A, CCDC168, ZNF527, HRAS, FAT1, OR7G3, WNT11, WNT10A, WNT3, WNT7A, and DTX3L, preferably from the group of Notch1, Notch2, Notch3, FAM58A, FLJ43860, CDKN2A, CCDC168, ZNF527, HRAS, FAT1, OR7G3, and DTX3L.
48. Use of a compound selected from the table 1 as a biomarker.
49. Use of a compound selected from the group of Notch1, Notch2, Notch3, AXIN2, LEF1, NKD1, SFRP2, FRZB, SFRP4, DKK2, FAM58A, FLJ43860, CDKN2A, OR7G3, WNT11, WNT10A, WNT3, WNT7A, and DTX3L, as a biomarker.
50. Use of a compound selected from the group of Notch1, Notch2, Notch3, SFRP2, FRZB, SFRP4 and DKK2, as a biomarker.
51. Use of a compound selected from the group of Notch1, Notch2 and Notch3 as a biomarker.
52. Use of a compound Notch1 as a biomarker.
53. Use of a compound selected from the group of Notch1, Notch2, Notch3, SFRP2, FRZB, SFRP4, DKK2, FAM58A, FLJ43860, CDKN2A, CCDC168, ZNF527, HRAS, FAT1, OR7G3, WNT11, WNT10A, WNT3 and WNT7A, as a biomarker.
54. Use of a compound selected from the group of Notch1, Notch2, Notch3, AXIN2, LEF1, NKD1, SFRP2, FRZB, SFRP4, DKK2, FAM58A, FLJ43860, CDKN2A, CCDC168, ZNF527, HRAS, FAT1, OR7G3, WNT11, WNT10A, WNT3, WNT7A and DTX3L, as a biomarker.
55. Use of a compound HRAS or FAT1 as a biomarker.
56. Use of a compound selected from the group consisting of FAM58A, FLJ43860, NOTCH1, OR7G3, CCDC168, ZNF527 and CDKN2A as a biomarker.
57. Use of a compound selected from the group of Notch1, Notch2, Notch3, FAM58A, FLJ43860, CDKN2A, CCDC168, ZNF527, HRAS, FAT1, OR7G3, WNT11, WNT10A, WNT3, WNT7A, and DTX3L, preferably from the group of Notch1, Notch2, Notch3, FAM58A, FLJ43860, CDKN2A, CCDC168, ZNF527, HRAS, FAT1, OR7G3, and DTX3L, as a biomarker.
58. Use of a compound according to any one of items 48 to 57, wherein the use indicates sensitivity of a cancer patient for treatment with a Wnt inhibitor.
59. Any one of items 39 to 42, 44 to 51, or 53 to 58, wherein at least two biomarkers, at least three or at least four biomarkers, are used to indicate together sensitivity of a cancer patient for treatment with a Wnt inhibitor.
60. Any one of items 1 to 59, wherein
WNT11, WNT10A, WNT3 or WNT7A expression in a patient sample is higher compared to a control, said expression indicates patient sensitivity for treatment with a Wnt inhibitor;
AXIN2, LEF1 or NKD1 expression in a patient sample is decreased after treatment compared to a pretreatment a control, said expression indicates patient sensitivity for treatment with a Wnt inhibitor;
Notch1, Notch2 or Notch3 expression is reduced, particularly activity or function is decreased increased in a patient sample compared to a control, said expression, particularly decrease of activity or function, indicates patient sensitivity for treatment with a Wnt inhibitor;
SFRP2, FRZB, SFRP4 or DKK2 expression in a patient sample is lower compared to a control, said expression indicates patient sensitivity for treatment with a Wnt inhibitor;
FAM58A, FLJ43860, CDKN2A, CCDC168, ZNF527, FAT1, OR7G3 or DTX3L expression is lower, particularly loss of function is higher, in a patient sample compared to a control, said expression, particularly loss of function, indicates patient sensitivity for treatment with a Wnt inhibitor;
HRAS expression is higher, particularly gain in function, in a patient sample compared to a control, indicates patient sensitivity for treatment with a Wnt inhibitor.
61. The item 60, wherein the Wnt inhibitor is as defined in any one of items 35 to 37.

DESCRIPTION OF THE DRAWINGS

FIG. 1A shows the structure of COMPOUND A. FIG. 1B shows the structure of COMPOUND B.

As shown in FIG. 4, COMPOUND A potently attenuated the abundance of HA-Wnt3A in the supernatant while sparing the lysate HA-Wnt3A, suggesting that Wnt3A secretion was substantially inhibited by COMPOUND A in a dose dependent manner.

FIG. 5A demonstrates that COMPOUND A indeed strongly blocked Wnt dependent phosphorylation of LRP6 in autocrine L-Wnt3A cells, a mouse mammary cell line overexpressing Wnt3A. FIG. 5B shows that the residues around the putative Wnt palmitoylation site, Ser209, are conserved among all 19 Wnts (SEQ ID NOS 2-20, respectively, in order of appearance). FIG. 5C shows that COMPOUND A demonstrated comparable inhibitory activities against all tested Wnts, including Wnt1, 2, 3, 3A, 6, 7A, and 9A.

As shown in FIG. 6, head and neck cancer cell (HNSCC) lines are among the top cancer types that were responsive to COMPOUND A.

FIG. 7 shows that among the HNSCC cell lines, 31 out of 96 showed Wnt pathway inhibition upon the treatment of COMPOUND A.

FIG. 8A shows that COMPOUND A potently inhibited Wnt-dependent AXIN2 production in HN30 with an IC50 of 0.3 nM. FIG. 8B depicts that COMPOUND A strongly attenuated HN30 colony formation albeit with a right-shifted IC50.

FIG. 9A shows that the reduced colony formation effect of COMPOUND A could be partially rescued with overexpression of dominant β-catenin. FIG. 9B confirms that the cellular effect of COMPOUND A was consistent to the inhibition of PORCN-dependent Wnt signaling activities; shRNA against PORCN substantially inhibited the expression of the Wnt target gene AXIN2. FIG. 9C shows that shRNA against PORCN also inhibited the colony formation of HN30 cells in vitro.

FIG. 10 shows in vivo anti-tumor activity of COMPOUND A; i.e. in a mouse subcutaneous xenograft model of HNSCC HN30. When dosed once a day the COMPOUND A induced dose-dependent efficacy and reduced tumor weight (FIG. 10A). After a single dose of COMPOUND A at 3 mg/kg, the levels of AXIN2 mRNA expression in tumors were reduced by ~60-95% between 5 and 10 hours post dose (FIG. 10B). Additionally, as shown in FIG. 10C, pLRP6 levels in the HN30 tumors were substantially reduced in a time dependent manner.

FIG. 11 The top oncogenes or tumor suppressor genes mutated in the set of HNSCC cell lines.

FIG. 12 The top candidate genes whose aggregated loss of function mutations correlated the best with the COMPOUND A PD response data from the HNSCC cell lines FIG. 13A and FIG. 13B show highly enriched Notch1 loss of function (LoF) mutation in COMPOUND A responsive head and neck cancer cell lines. FIG. 13A) Diagrams of potential LoF mutations of Notch1 in head and neck cancer cell lines, N: N-terminus: C: C-terminus; LNR: Lin12-Notch repeat; TMD: Transmembrane domain; PEST: Proline, glutamic acid, serine, threonine-rich (PEST) domain. Frame shift (fs) and nonsense mutations (X) include E488fs, A495fs, K538fs, G192X, P460fs, E216X, are highlighted in red. FIG. 13B) The list of Notch1 frameshift and nonsense mutations in head and neck cancer cell lines. FIG. 13C) Notch1 C478F showed complete reduction of activities compared with the wild-type, in a Notch1 reporter gene assay with or without DLL1 stimulation.

FIG. 14 shows in vivo efficacy of the COMPOUND A. In a SNU1076 xenograft model in mice, COMPOUND A at the dose of 5 mg/kg significantly inhibited the tumor growth (T/C: 25%) after 14 days of treatment (FIG. 14A). COMPOUND A substantially inhibited the Wnt pathway as indicated by 70% reduction of AXIN2 (FIG. 14B).

FIG. 15 shows FAT1 mutations in the head neck cancer cell lines. FAT1 mutations are enriched in COMPOUND A responsive head neck cancer cell lines.

FIG. 16 shows HRAS mutations in the head neck cancer cell lines. HRAS mutations are enriched in COMPOUND A responsive head neck cancer cell lines.

DESCRIPTION OF THE INVENTION

Definitions

Figure 2A:
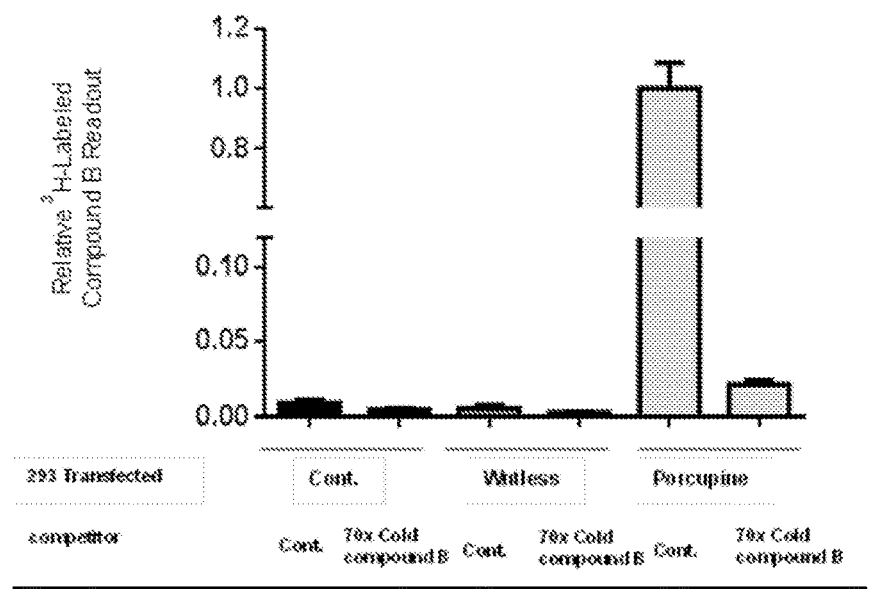
FIG. 2A shows the binding of $^3$H-radiolabelled compound B to PORCN. The specific interaction between COMPOUND B and PORCN could be competed off by unlabeled COMPOUND B (FIG. 2A).

As used in the specification and claims, the singular form "a", an and "the" include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." It also is to be understood, although not always explicitly stated, that the reagents described herein are merely exemplary and that equivalents of such are known in the art.

The terms "marker" or "biomarker" are used interchangeably herein. A biomarker is a nucleic acid or polypeptide and the presence, absence or differential expression of the nucleic acid or polypeptide, the parameter describing the gene number, gene or protein mutation, function, or activity and is used to determine sensitivity to any Wnt inhibitor. For example, Notch1 is a biomarker and the mRNA expression of Notch1 in a cancer sample cell is decreased when compared to Notch1 expression in normal (non-cancerous) tissue or control tissue.

"PORCN" refers to Porcupine, a membrane-bound acyltransferase, required for Wnt post-translational modification. Unless specifically stated otherwise, PORCN as used herein, refers to human PORCN-accession numbers NM_017617.3/NP_060087 (4851/P46531.4).

"Notch1" refers to Notch homolog 1. It is a single pass transmembrane receptor in Notch signaling. Unless specifically stated otherwise, Notch1 as used herein refers to human Notch1-accession numbers NM_017617.3/NP_060087/GI:148833508 (4851/P46531.4). "Notch2" refers to neurogenic locus notch homolog protein 2, a single pass transmembrane receptor in Notch signaling. Unless specifically stated otherwise, Notch2 as used herein refers to human Notch2-accession numbers NM_024408.3/NP_077719/GI:24041035 (4853/Q04721.3). "Notch3" refers to neurogenic locus notch homolog protein 3, a single pass transmembrane receptor in Notch signaling. Unless specifically stated otherwise, Notch3 as used herein refers to human Notch3-accession numbers NM_000435.2/NP_000426/GI:134244285 (4854/Q9UM47.2).

"AXIN2" refers to axis inhibition protein 2. It is a cytosolic protein with an important role in the regulation of the stability of beta-catenin. Unless specifically stated otherwise, AXIN2 as used herein refers to human AXIN2-accession numbers NM_004655.3/NP_004646/GI:195927059 (8313/Q9Y2T1)

"LEF1" refers to lymphoid enhancer-binding factor-1. It is a nuclear protein forming a complex with β-catenin and driving down stream target gene expression. Unless specifically stated otherwise, LEF1 as used herein, refers to human LEF1-accession numbers NM_016269/NP_001124185/GI:7705917 (51176/Q9UJU2.1)

"NKD1" refers to naked cuticle 1. It is a cytosolic protein interacting with Disheveled. Unless specifically stated otherwise, NKD1 as used herein, refers to human NKD1-accession numbers NM_033119/NP_149110/GI:14916433 (85407/Q969G9.1)

"SFRP2" refers to secreted frizzled-related protein 2. It is a soluble modulator of Wnt signaling. Unless specifically stated otherwise, SFRP2 as used herein, refers to human SFRP2-accession numbers NM_003013.2/NP_003004/GI:48475052 (6423/Q96HF1.2)

"FRZB" refers to frizzled-related protein, also a soluble modulator of Wnt signaling. Unless specifically stated otherwise, FRZB as used herein, refers to human FRZB-accession numbers NM_001463.3/NP_001454/GI:38455388 (2487/Q92765.2)

"SFRP4" refers to secreted frizzled-related protein 4, also a soluble modulator of Wnt signaling. Unless specifically stated otherwise, SFRP4 as used herein, refers to human SFRP4-accession numbers NM_003014.3/NP_003005/GI:170784838 (6424/Q6FHJ7.2)

"DKK2" refers to dickkopf-related protein 2, also a soluble modulator of Wnt signaling. Unless specifically stated otherwise, DKK2 as used herein, refers to human DKK2-accession numbers NM_014421.2/NP_055236/GI:7657023 (27123/Q9UBU2.1)

"WNT11" refers to WNT 11. It is a secreted Wnt ligand protein. Unless specifically stated otherwise, WNT11 as used herein, refers to human WNT11-accession numbers NM_004626.2/NP_004617/GI:17017974 (7481/O96014)

"WNT10A" refers to WNT10A, also a secreted Wnt ligand protein. Unless specifically stated otherwise, WNT10A as used herein, refers to human WNT10A-accession numbers NM_025216.2/NP_079492/GI:16936520 (80326/Q9GZT5).

"WNT3" refers to WNT3, also a secreted Wnt ligand protein. Unless specifically stated otherwise, WNT3 as used herein, refers to human WNT3-accession numbers NM_030753.3/NP_110380/GI:13540477 (7473/P56703)

"WNT7A" refers to WNT7A, also a secreted Wnt ligand protein. Unless specifically stated otherwise, WNT7A as used herein, refers to human WNT7A-accession numbers NM_004625.3/NP_004616/GI:17505191 (7476/O00755)

"FAM58A" refers to family with sequence similarity 58, member A. This gene contains a cyclin-box-fold domain, may have a role in controlling nuclear cell division cycles. Unless specifically stated otherwise, FAM58A as used herein, refers to human FAM58A-accession numbers NM_152274.3/NP_689487/GI:196049382 (92002/Q8N1B3).

"FLJ43860" refers to FLJ43860 protein, a uncharacterized protein with unknown function. Unless specifically stated otherwise, FLJ43860 as used herein refers to human FLJ43860-accession numbers NM_207414.2/NP_997297/GI:148727311 (389690/Q6ZUA9).

"CDKN2A" refers to Cyclin-dependent kinase inhibitor 2A, a key inhibitor for cell cycle progression. Unless specifically stated otherwise, CDKN2A as used herein refers to human CDKN2A-accession numbers NM_000077.4/NP_478104/GI:4502749 (1029/P42771).

"OR7G3" refers to Olfactory receptor 7G3, one of the olfactory G-protein-coupled receptor (GPCR) receptors. Unless specifically stated otherwise, OR7G3 as used herein refers to human OR7G3-accession numbers NM_001001958.1/NP_001001958/GI:50080201 (390883/Q8NG95).

"DTX3L" refers to Deltex 3-like, an E3 ubiquitin ligase, its *Drosophila* homologue Deltex is a positive regulator of Notch signaling in *Drosophila*. Unless specifically stated otherwise, DTX3L as used herein refers to human DTX3L-accession numbers NM_138287.3/NP_612144.1/GI:19923717 (151636/Q8TDB6).

"CCDC168" refers to coiled-coil domain containing 168, is a protein with coiled-coil domains. Unless specifically stated otherwise, CCDC168 as used herein refers to human CCDC168-accession numbers NM_001146197.1/NP_001139669.1/GI:226246553 (643677/Q8NDH2).

"ZNF527" refers to Zinc finger protein 527, belong to the zinc finger protein family. Unless specifically stated otherwise, ZNF527 as used herein refers to human ZNF527-accession numbers NM_032453.1/NP_115829/GI:149192840 (84503/Q8NB42).

"HRAS" refers to Harvey rat sarcoma viral oncogene homolog, is a small G protein, activating the MAP kinase pathway. Unless specifically stated otherwise, HRAS as used herein refers human HRAS-accession numbers NM_005343.2/NM_176795.3 NM_001130442.1/NP_001123914.1/GI:47117697/GI:194363760/GI:194363761 (3265/P01112).

"FAT1" refers to FAT1, is a protocadherin protein, reported to bind to β-catenin and prevent its nuclear translocation. Unless specifically stated otherwise, FAT1 refers to human FAT1-accession numbers NM_005245.3/NP_005236/GI:75813622 (2195/Q14517).

Herein, only one gene accession number was listed for any given gene. It should be understood that any splicing form associated with the gene is contemplated by the present disclosure. By a splicing form it is meant herein a mRNA from a single gene being spliced in alternative ways which results in the expression of multiple protein variants from a single gene. For example, Notch2 has two splicing variants, NM_024408 and NM_001200001. Only NM_024408 was listed for Notch2.

"Sensitivity" as used herein means that a cell or a patient responds to a Wnt inhibitor in a sense that tumor growth, invasiveness or metastasis is delayed, stopped, suppressed or tumor shrinkage or regression is achieved, due to the effect of the Wnt inhibitor. In one embodiment of the invention, a cell or patient sample has "sensitivity" to a Wnt inhibitor if the cell or patients sample responds to treatment with a more than 50% Axin2 reduction (Wnt pathway inhibition), e.g. reduction of Axin2 mRNA or protein levels, when the cell or patient sample is treated with 10-100 nM of COMPOUND A over 48 hours. In a specific embodiment, a cell or patient sample has "sensitivity" to a Wnt inhibitor if the cell or patients sample responds to treatment with a more than 50% reduction in Axin2 mRNA level, when the cell or patient sample is treated with 50 nM of COMPOUND A over 48 hours.

A cell is "sensitive" or displays "sensitivity" for inhibition with an Wnt inhibitor when at least one of the biomarkers selected from Table 1 is differentially downregulated compared to a control. Alternatively, a cell is "sensitive" for inhibition with a Wnt inhibitor when more than one, more than two, more than three, or the whole set of the biomarkers are differentially expressed.

A "control cell" or "normal cell" refers to non-cancerous tissue or cell.

A "control tissue" or "normal tissue" refers to non-cancerous tissue or cell.

A "control sample" or "normal sample" refers to non-cancerous tissue or cell.

"Control" as used herein is the biomarker expression in a control cell, control tissue or control sample, or a parameter or a numerical value that describes a value that correlates well with normal or healthy biomarker expression, i.e. biomarker expression in a normal, non-cancerous cell, sample or tissue.

A Notch1 "extracellular domain" denotes herein the Notch1 region of amino acids 1 to 1735.

The terms "nucleic acid" and "polynucleotide" are used interchangeably and refer to a polymeric form of nucleotides of any length, either deoxyribonucleotides or ribonucleotides or analogs thereof. Polynucleotides can have any three-dimensional structure and may perform any function. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A "gene" refers to a polynucleotide containing at least one open reading frame (ORF) that is capable of encoding a particular polypeptide or protein after being transcribed and translated. A polynucleotide sequence can be used to identify larger fragments or full-length coding sequences of the gene with which they are associated. Methods of isolating larger fragment sequences are known to those of skill in the art.

"Gene expression", "gene product" or "expression" are all used herein interchangeably and refer to the nucleic acids or amino acids (e.g., peptide or polypeptide) generated when a gene is transcribed and translated, DNA copy number of the biomarker, genomic DNA, cDNA or RNA sequence of the biomarker; biomarker gene expression, biomarker protein expression, biomarker mRNA expression; functional effect of the biomarker protein; functional effect of the biomarker gene, cDNA or mRNA; protein, cDNA, gene or mRNA activity, or loss thereof, or mutation status like for example frame-shift mutation, deletion, translocation, insertion, duplication, inversion, functional mutation; or combinations thereof.

In a particular embodiment "gene expression", "gene product" or "expression" denote DNA expression, DNA copy number, mRNA expression, cDNA expression, protein transcription, protein expression, DNA modification, cDNA modification, mRNA modification, protein modification, DNA function, cDNA function, mRNA function, protein function, DNA mutation, cDNA mutation, mRNA mutation, protein mutation, or combinations thereof; preferably is DNA mutation. DNA modification includes DNA alkylation or acylation. For example, methylation is a biochemical process involving the addition of a methyl group to the cytosine or adenine DNA nucleotides. mRNA modification includes RNA editing, which is a biochemical process involving the change of nucleotides after they have been generated by RNA polymerase to form a sequence. cDNA modification includes any modification that was made at the mRNA level will be translated into cDNA modification. Protein modification includes a biochemical process involving the change of amino acids after they have been translated. Protein function is understood for proteins to carry out the duties specified by the information encoded in genes, including facilitation of signalling transduction, enzymatic reactions etc.

The term "polypeptide" is used interchangeably with the term "protein" and in its broadest sense refers to a compound of two or more subunit amino acids, amino acid analogs, or peptidomimetics. The subunits can be linked by peptide bonds. In another embodiment, the subunit may be linked by other bonds, e.g., ester, ether, etc.

As used herein the term "amino acid" refers to either natural and/or unnatural or synthetic amino acids, and both the D and L optical isomers, amino acid analogs, and peptidomimetics. A peptide of three or more amino acids is commonly called an oligopeptide if the peptide chain is short. If the peptide chain is long, the peptide is commonly called a polypeptide or a protein.

The term "isolated" means separated from constituents, cellular and otherwise, in which the polynucleotide, peptide, polypeptide, protein, antibody or fragment(s) thereof, are normally associated with in nature. For example, an isolated polynucleotide is separated from the 3' and 5' contiguous nucleotides with which it is normally associated within its native or natural environment, e.g., on the chromosome. As is apparent to those of skill in the art, a non-naturally occurring polynucleotide, peptide, polypeptide, protein, antibody, or fragment(s) thereof, does not require "isolation" to distinguish it from its naturally occurring counterpart. In addition, a "concentrated," "separated" or "diluted" polynucleotide, peptide, polypeptide, protein, antibody or fragment(s) thereof, is distinguishable from its naturally occurring counterpart in that the concentration or number of molecules per volume is greater in a "concentrated" version or less than in a "separated" version than that of its naturally occurring counterpart. A polynucleotide, peptide, polypeptide, protein, antibody, or fragment(s) thereof, which differs from the naturally occurring counterpart in its primary sequence or, for example, by its glycosylation pattern, need not be present in its isolated form since it is distinguishable from its naturally occurring counterpart by its primary sequence or, alternatively, by another characteristic such as glycosylation pattern. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in PCR: A Practical Approach, M. MacPherson et al., IRL Press at Oxford University Press (1991). All processes of producing replicate copies of a polynucleotide, such as PCR or gene cloning, are collectively referred to herein as "replication." A primer can also be used as a probe in hybridization reactions, such as Southern or Northern blot analyses (Sambrook et al., Molecular Cloning: A Laboratory Manual, 2nd edition (1989)).

"Differential expressed" as used herein means a measurable difference in expression, normally when compared to a control. For example, when applied to a gene, it can refer to the differential mutation status of a gene compared to a normal, wildtype, functional gene in a normal cell. A differentially mutated gene can be mutated as compared to the wildtype gene, which causes loss of function of the mutated gene. It can also refer to the differential production of the mRNA transcribed and/or translated from the gene or the protein product encoded by the gene. A differentially expressed gene may be overexpressed or underexpressed as compared to the expression level of a normal or control cell. However, as used herein, overexpression is an increase in gene expression and generally is at least 1.25 fold or, alternatively, at least 1.5 fold or, alternatively, at least 2 fold, or alternatively, at least 3 fold or alternatively, at least 4 fold expression over that detected in a normal or control counterpart cell or tissue. As used herein, underexpression, is a reduction of gene expression and generally is at least 1.25 fold, or alternatively, at least 1.5 fold, or alternatively, at least 2 fold or alternatively, at least 3 fold or alternatively, at least 4 fold expression under that detected in a normal or control counterpart cell or tissue. The term "differentially expressed" also refers to where expression in a cancer cell or cancerous tissue is different compared to the expression in a control (for example control cell or normal tissue, e.g. non-cancerous cell or tissue). As an example, the biomarker is differentially expressed or differentially downregulated if the expression in a cancer sample is at least 1.25 fold, or alternatively, at least 1.5 fold, or alternatively, at least 2 fold or alternatively, at least 3 fold or alternatively, at least 4 fold lower compared to the expression in a control.

A high expression level of the gene may occur because of over expression of the gene or an increase in gene copy number. The gene may also be translated into increased protein levels because of deregulation or absence of a negative regulator.

The term "cDNA" refers to complementary DNA, i.e. mRNA molecules present in a cell or organism made into cDNA with an enzyme such as reverse transcriptase. A "cDNA library" is a collection of all of the mRNA molecules present in a cell or organism, all turned into cDNA molecules with the enzyme reverse transcriptase, then inserted into "vectors" (other DNA molecules that can continue to replicate after addition of foreign DNA). Exemplary vectors for libraries include bacteriophage (also known as "phage"), viruses that infect bacteria, for example, lambda phage. The library can then be probed for the specific cDNA (and thus mRNA) of interest.

As an example, transcriptional activity can be assessed by measuring levels of messenger RNA using a gene chip such as the Affymetrix® HG-U133-Plus-2 GeneChips. High-throughput, real-time quantitation of RNA of a large number of genes of interest thus becomes possible in a reproducible system.

The terms "stringent hybridization conditions" refers to conditions under which a nucleic acid probe will specifically hybridize to its target subsequence, and to no other sequences. The conditions determining the stringency of hybridization include: temperature, ionic strength, and the concentration of denaturing agents such as formamide. Varying one of these factors may influence another factor and one of skill in the art will appreciate changes in the conditions to maintain the desired level of stringency. An example of a highly stringent hybridization is: 0.015M sodium chloride, 0.0015M sodium citrate at 65-68° C. or 0.015M sodium chloride, 0.0015M sodium citrate, and 50% formamide at 42° C. (see Sambrook, supra). An example of a "moderately stringent" hybridization is the conditions of: 0.015M sodium chloride, 0.0015M sodium citrate at 50-65° C. or 0.015M sodium chloride, 0.0015M sodium citrate, and 20% formamide at 37-50° C. The moderately stringent conditions are used when a moderate amount of nucleic acid mismatch is desired. One of skill in the art will appreciate that washing is part of the hybridization conditions. For example, washing conditions can include 0.2×-0.1×SSC/0.1% SDS and temperatures from 42-68° C., wherein increasing temperature increases the stringency of the wash conditions.

When hybridization occurs in an antiparallel configuration between two single-stranded polynucleotides, the reaction is called "annealing" and those polynucleotides are described as "complementary." A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

A polynucleotide or polynucleotide region (or a polypeptide or polypeptide region) has a certain percentage (for example, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Current Protocols in Molecular Biology, Ausubel et al., eds., (1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cut-off=60; expect=10; Matrix=BLOSUM62; Descriptions=50 sequences; sort by=HIGH SCORE; Databases=non-redundant.

The biomarker herein includes gene variants and genes with at least 95% sequence identity.

The term "cell proliferative disorders" shall include dysregulation of normal physiological function characterized by abnormal cell growth and/or division or loss of function. Examples of "cell proliferative disorders" include but are not limited to hyperplasia, neoplasia, metaplasia, and various autoimmune disorders, e.g., those characterized by the dysregulation of T cell apoptosis.

As used herein, the terms "neoplastic cells," "neoplastic disease," "neoplasia," "tumor," "tumor cells," "cancer," and "cancer cells," (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign. A metastatic cell or tissue means that the cell can invade and destroy neighboring body structures.

"Head and neck cancer" or "head and neck squamous cell carcinoma" are used interchangeably and refer to a cancer that arises in the head or neck region[16]. Primarily it is a cancer of the nasal cavity, sinuses, lips, mouth, salivary glands, throat, or larynx. 90 percent of head and neck cancers are classified as head and neck squamous cell carcinoma. It is the sixth leading cancer by incidence worldwide, with approximately 600,000 cases per year worldwide. And 5-year survivor rate for HNSCC patients is around 40-50%.

"Suppressing tumor growth" indicates a reduction in tumor cell growth, which can be assessed by any means known in the art, including, but not limited to, measuring tumor size, determining whether tumor cells are proliferating using a 3H-thymidine incorporation assay, measuring glucose uptake by FDG-PET (fluorodeoxyglucose positron emission tomography) imaging, or counting tumor cells. "Suppressing" tumor cell growth means any or all of the following states: slowing, delaying and stopping tumor growth, as well as tumor shrinkage.

A "pharmaceutical composition" is a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives, for example; proteins, peptides, amino acids, lipids, and carbohydrates (e.g., sugars, including monosaccharides and oligosaccharides; derivatized sugars such as alditols, aldonic acids, esterified sugars and the like; and polysaccharides or sugar polymers), which can be present singly or in combination, comprising alone or in combination 1-99.99% by weight or volume. Carbohydrate excipients include, for example; monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like.

The term "carrier" further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-quadrature-cyclodextrin), polyethylene glycols, flavoring agents, antimicrobial agents, sweeteners, antioxidants, antistatic agents, surfactants (e.g., polysorbates such as TWEEN 20™ and TWEEN 80™), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional provision that they be acceptable for use in vivo. For examples of carriers, stabilizers and adjuvants, see Remington's Pharmaceutical Science, 15th Ed. (Mack Publ. Co., Easton (1975) and in the Physician's Desk Reference, 52nd ed., Medical Economics, Montvale, N.J. (1998).

An "effective amount" is an amount sufficient to effect beneficial or desired results in a sensitive cell or patient sample, e.g. prevents tumor growth. It can also denote an amount that inhibits the Wnt pathway. An effective amount can be administered in one or more administrations, applications or dosages.

A "subject," "individual" or "patient" is used interchangeably herein, which refers to a vertebrate, preferably a mammal, more preferably a human. Mammals include, but are not limited to, mice, simians, humans, farm animals, sport animals, and pets.

An "Wnt inhibitor" as used herein reduces the activity of Wnt pathway. Wnt inhibitors are compounds which can inhibit the Wnt signaling pathways, and include the PORCN inhibitors. This inhibition may include, for example, inhibiting PORCN, and its palmitoylation of Wnt, or reducing the association between the Wnt pathway components including Frizzled and Disheveled. Preferably a Wnt inhibitor is a PORCN inhibitor.

In a particular embodiment the Wnt inhibitor used for the treatment as described herein is any suitable compound as disclosed in the WO2010/101849 A1 (PCT/US10/025813), preferably a compound of Formula (1):

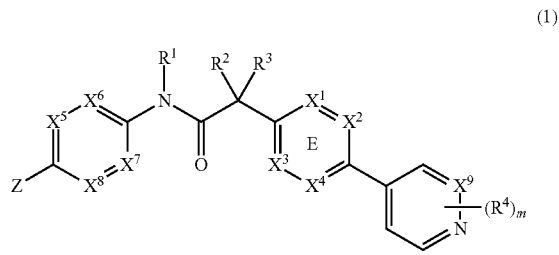

(1)

or a physiologically acceptable salt thereof, wherein:
wherein $X^1$, $X^2$, $X^3$ and $X^4$ is selected from N and $CR^7$;
one of $X^5$, $X^6$, $X^7$ and $X^8$ is N and the others are CH;
$X^9$ is selected from N and CH;
Z is selected from phenyl, pyrazinyl, pyridinyl, pyridazinyl and piperazinyl; wherein each phenyl, pyrazinyl, pyridinyl, pyridazinyl or piperazinyl of Z is optionally substituted with an
$R^6$ group;
$R^1$, $R^2$ and $R^3$ are hydrogen;
m is 1;
$R^4$ is selected from hydrogen, halo, difluoromethyl, trifluoromethyl and methyl;
$R^6$ is selected from hydrogen, halo and —C(O)$R^{10}$; wherein $R^{10}$ is methyl; and
$R^7$ is selected from hydrogen, halo, cyano, methyl and trifluoromethyl.

Particularly the Wnt inhibitor can be a compound selected from the group of N-[5-(3-fluorophenyl)pyridin-2-yl]-2-[5-methyl-6-(pyridazin-4-yl)pyridin-3-yl]acetamide;
2-[5-methyl-6-(2-methylpyridin-4-yl)pyridin-3-yl]-N-[5-(pyrazin-2-yl)pyridin-2-yl]acetamide;
N-(2,3'-bipyridin-6'-yl)-2-(2',3-dimethyl-2,4'-bipyridin-5-yl)acetamide;
N-(5-(4-acetylpiperazin-1-yl)pyridin-2-yl)-2-(2'-methyl-3-(trifluoromethyl)-2,4'-bipyridin-5-yl)acetamide;
N-(5-(4-acetylpiperazin-1-yl)pyridin-2-yl)-2-(2'-fluoro-3-methyl-2,4'-bipyridin-5-yl)acetamide; and
2-(2'-fluoro-3-methyl-2,4'-bipyridin-5-yl)-N-(5-(pyrazin-2-yl)pyridin-2-yl)acetamide;
or a pharmaceutically acceptable salt thereof.
In a separate embodiment the Wnt inhibitor is 2-[5-methyl-6-(2-methylpyridin-4-yl)pyridin-3-yl]-N-[5-(pyrazin-2-yl)pyridin-2-yl]acetamide (compound A).
Further Wnt inhibitor as disclosed in WO2011/123785 (PCT/US2011/030950) or WO2011/088123 (PCT/US2011/020994) can be used according to the present disclosure.

DETAILED DESCRIPTION OF THE INVENTION

A number of genes have now been identified that can serve as a biomarker for a Wnt inhibitor. They are listed in Table 1. These biomarkers can be used to determine the sensitivity of cancer patients to the inhibitor and help monitor the response of those patients receiving the therapeutic. Furthermore, well defined biomarkers can indicate which patient should receive a therapeutic, i.e. can be used for patient stratification and increase the chances that the compound will eventually elicit response in a patient. They allow for more timely and aggressive treatment as opposed to a trial and error approach. The biomarkers can also be used for monitoring the effectiveness of the treatment. If biomarkers indicate that the patient has become insensitive to the treatment, then the dosage administered can be increased, decreased, completely discontinued or an additional therapeutic administered. As such, the identified biomarkers, i.e. any biomarker selected from Table 1 is a suitable biomarker associated with Wnt inhibitors or PORCN inhibitors. The approach of using the biomarkers ensures that the correct patients receive the appropriate treatment and during the course of the treatment the patient can be monitored for continued Wnt, particularly PORCN, inhibitor sensitivity. Cancer patient in the method of treatment can get selectively treated depending on their sensitivity to the Wnt inhibitor. The biomarkers were identified by conducting experiments in cell lines and mouse xenografts, or determined based on the bioinformatics analysis.

The decrease of gene expression of one or more of the biomarkers identified herein can be used to determine patient sensitivity to any Wnt inhibitor, for example, the decrease or overexpression of a biomarker indicates that a cancer patient is sensitive to and would favorably respond to administration of an Wnt inhibitor, particularly compound A. As another example, after treatment with a Wnt inhibitor, a patient sample can be obtained and the sample assayed for sensitivity to discover if the patient is still sensitive to the treatment with a Wnt inhibitor. Alternatively, a combination of more than one biomarker selected from Table 1 can be assayed to get the result. The treatment with a Wnt inhibitor, particularly those as defined herein, specifically compound A, can be selective. This means that only those patients that are identified as sensitive or as those that are likely to respond to the treatment with a Wnt inhibitor, receive a Wnt inhibitor. Others can optionally receive an alternative treatment with other drug.

It has been determined that variations of gene expression of said biomarkers, including loss or gain of activity or function, in a patient sample before treatment or after treatment, as compared to a control sample, can indicate that a patient responds to treatment with a Wnt inhibitor. For example the Wnt inhibitor can be the compound A. More specifically, a higher expression of WNT11, WNT10A, WNT3, WNT7A in a patient sample compared to a control indicates patient's likely sensitivity to treatment with a Wnt inhibitor. On the other hand, patient's likely sensitivity to treatment with a Wnt inhibitor is indicated by a decreased expression of AXIN2, LEF1, NKD1 compared to a control expression. If Notch1, Notch2 or Notch3 expression is reduced, or particularly if their activity or function is decreased when compared to a control, it indicates patient's likely sensitivity for treatment with a Wnt inhibitor. Said activity or function can be caused by a mutation. A detection of lower SFRP2, FRZB, SFRP4 or DKK2 expression in a patient sample when compared to a control can indicate patient sensitivity for treatment with a Wnt inhibitor. Lower expression of FAM58A, FLJ43860, CDKN2A, CCDC168, ZNF527, FAT1, OR7G3 or DTX3L, particularly their loss of function, when compared to a control levels, can indicate that patients will likely respond to treatment with a Wnt inhibitor. When a patient sample shows higher expression of HRAS, particularly a gain in function, when compared to a control, a patient sensitivity for treatment with a Wnt inhibitor is more likely.

It has been demonstrated that head neck cancer cells are highly responsive to Wnt inhibitors. Cancer patients having head and neck cancer can benefit from the treatment with a Wnt inhibitor. In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day. Suitable unit dosage forms for oral administration comprise from ca. 1 to 50 mg active ingredient.

Particularly can benefit from the treatment with a Wnt inhibitor, preferably COMPOUND A, patients having head and neck cancer that harbors differential downregulated expression of the biomarker selected from Table 1 compared to a control. The chance that such a patient responds is the highest. By the same token the patient suffering from other tumor types could also be treated, as long as differential expression of the biomarker selected from Table 1 is downregulated in their cancer sample compared to a control. Once treatment with the Wnt inhibitor starts, the effectiveness of the inhibitor can be monitor by comparing differential expression of Axin2, LEF1 and/or NKD1 to the expression in a cancer sample that is sensitive to a Wnt inhibitor. Normally, the expression of Axin2, LEF1 and/or NKD1 gets downregulated, if Wnt inhibitor is effective. Insufficiently downregulated expression of Axin2, LEF1 and/or NKD1 is indicative for a need of dose adjustment, or may necessitate combining the Wnt inhibitor with another anti-tumor agent.

Measurement of Gene Expression

Detection of gene expression can be by any appropriate method, including for example, detecting the quantity of mRNA transcribed from the gene or the quantity of cDNA produced from the reverse transcription of the mRNA transcribed from the gene or the quantity of the polypeptide or protein encoded by the gene. These methods can be performed on a sample by sample basis or modified for high throughput analysis. For example, using Affymetrix™ U133 microarray chips.

In one aspect, gene expression is detected and quantitated by hybridization to a probe that specifically hybridizes to the appropriate probe for that biomarker. The probes also can be attached to a solid support for use in high throughput screening assays using methods known in the art. WO 97/10365 and U.S. Pat. Nos. 5,405,783, 5,412,087 and 5,445,934, for example, disclose the construction of high density oligonucleotide chips which can contain one or more of the sequences disclosed herein. Using the methods disclosed in U.S. Pat. Nos. 5,405,783, 5,412,087 and 5,445,934, the probes of this invention are synthesized on a derivatized glass surface. Photoprotected nucleoside phosphoramidites are coupled to the glass surface, selectively deprotected by photolysis through a photolithographic mask, and reacted with a second protected nucleoside phosphoramidite. The coupling/deprotection process is repeated until the desired probe is complete.

In one aspect, the expression level of a gene is determined through exposure of a nucleic acid sample to the probe-modified chip. Extracted nucleic acid is labeled, for example, with a fluorescent tag, preferably during an amplification step. Hybridization of the labeled sample is performed at an appropriate stringency level. The degree of probe-nucleic acid hybridization is quantitatively measured using a detection device. See U.S. Pat. Nos. 5,578,832 and 5,631,734.

Alternatively any one of gene copy number, transcription, or translation can be determined using known techniques. For example, an amplification method such as PCR may be useful. General procedures for PCR are taught in MacPherson et al., PCR: A Practical Approach, (IRL Press at Oxford University Press (1991)). However, PCR conditions used for each application reaction are empirically determined. A number of parameters influence the success of a reaction. Among them are annealing temperature and time, extension time, Mg 2+ and/or ATP concentration, pH, and the relative concentration of primers, templates, and deoxyribonucleotides. After amplification, the resulting DNA fragments can be detected by agarose gel electrophoresis followed by visualization with ethidium bromide staining and ultraviolet illumination.

In one embodiment, the hybridized nucleic acids are detected by detecting one or more labels attached to the sample nucleic acids. The labels can be incorporated by any of a number of means well known to those of skill in the art. However, in one aspect, the label is simultaneously incorporated during the amplification step in the preparation of the sample nucleic acid. Thus, for example, polymerase chain reaction (PCR) with labeled primers or labeled nucleotides will provide a labeled amplification product. In a separate embodiment, transcription amplification, as described above, using a labeled nucleotide (e.g. fluorescein-labeled UTP and/or CTP) incorporates a label in to the transcribed nucleic acids.

Alternatively, a label may be added directly to the original nucleic acid sample (e.g., mRNA, polyA, mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., 3H, 125I, 35S, 14C, or 32P) enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Detection of labels is well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

The detectable label may be added to the target (sample) nucleic acid(s) prior to, or after the hybridization, such as described in WO 97/10365. These detectable labels are directly attached to or incorporated into the target (sample) nucleic acid prior to hybridization. In contrast, "indirect labels" are joined to the hybrid duplex after hybridization. Generally, the indirect label is attached to a binding moiety that has been attached to the target nucleic acid prior to the hybridization. For example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see Laboratory Techniques in Biochemistry and Molecular Biology, Vol. 24: Hybridization with Nucleic Acid Probes, P. Tijssen, ed. Elsevier, N.Y. (1993).

Detection of Polypeptides

Expression level of the biomarker can also be determined by examining protein expression or the protein product at least one of the biomarkers selected from Table 1. Determining the protein level involves measuring the amount of any immunospecific binding that occurs between an antibody that selectively recognizes and binds to the polypeptide of the biomarker in a sample obtained from a patient and comparing this to the amount of immunospecific binding of at least one biomarker in a control sample. The amount of protein expression of the biomarker can be increased or reduced when compared with control expression. Alternatively, a combination of more than one of the biomarkers selected from Table 1 can be assayed.

A variety of techniques are available in the art for protein analysis. They include but are not limited to radioimmunoassays, ELISA (enzyme linked immunosorbent assays), "sandwich" immunoassays, immunoradiometric assays, in situ immunoassays (using e.g., colloidal gold, enzyme or radioisotope labels), western blot analysis, immunoprecipitation assays, immunofluorescent assays, flow cytometry, immunohistochemistry, confocal microscopy, enzymatic assays, surface plasmon resonance and PAGE-SDS.

Assaying for Biomarkers and the Treatment with a Wnt Inhibitor

Once a patient has been predicted to be sensitive to an Wnt inhibitor, administration of any Wnt inhibitor to a patient can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents may be empirically adjusted.

At least one of the biomarkers selected from Table 1 can be assayed for after administration of a Wnt inhibitor in order to determine if the patient remains sensitive to the treatment with a Wnt inhibitor. In addition, at least one biomarker can be assayed for in multiple time points after a single administration of the inhibitor. For example, an initial bolus of a Wnt inhibitor is administered, at least one biomarker is assayed for at 1 hour, 2 hours, 3 hours, 4 hours, 8 hours, 16 hours, 24 hours, 48 hours, 3 days, 1 week or 1 month or several months after the first treatment. Alternatively, more than one, for example 2, 3, 4, 5 or all of the biomarkers selected from Table 1 can be assayed together.

The at least one biomarker selected from Table 1 can be assayed for after each administration of a Wnt inhibitor, so if there are multiple administrations of Wnt inhibitors, then at least one biomarker can be assayed for after each administration to determine continued patient sensitivity. The patient could undergo multiple administrations of a Wnt inhibitor and the biomarkers then assayed at different time points. For example, a course of treatment can require administration of an initial dose of a Wnt inhibitor, a second dose a specified time period later, and still a third dose hours after the second dose. At least one biomarker could be assayed for at 1 hour, 2 hours, 3 hours, 4 hours, 8 hours, 16 hours, 24 hours, 48 hours, 3 days, 1 week or 1 month or several months after administration of each dose of a Wnt inhibitor. Alternatively, more than one, for example 2, 3, 4, 5 or all of the biomarkers selected from Table 1 can be assayed together.

It is also within the scope of the invention that different biomarkers are assayed for at different time points. Without being bound to any one theory, due to mechanism of action of the Wnt inhibitor or of the biomarker, the response to the Wnt inhibitor is delayed and at least one biomarker is assayed for at any time after administration to determine if the patient remains sensitive to the administration of the drug. An assay for at least one biomarker selected from Table 1 after each administration of a Wnt inhibitor will provide guidance as to the means, dosage and course of treatment.

Finally, there is administration of different Wnt inhibitors and followed by assaying for at least one biomarker selected from Table 1. In this embodiment, more than one Wnt inhibitor is chosen and administered to the patient. At least one biomarker selected from Table 1 can then be assayed for after administration of each different Wnt inhibitor. As above, this assay can also be done at multiple time points after administration of the different Wnt inhibitors. For example, a first Wnt inhibitor could be administered to the patient and at least one biomarker assayed at 1 hour, 2 hours, 3 hours, 4 hours, 8 hours, 16 hours, 24 hours, 48 hours, 3 days, 1 week or 1 month or several months after administration. A second inhibitor could then be administered and at least one biomarker could be assayed for again at 1 hour, 2 hours, 3 hours, 4 hours, 8 hours, 16 hours, 24 hours, 48 hours, 3 days, 1 week or 1 month or several months after administration of the second Wnt inhibitor. Alternatively, more than one, for example 2, 3, 4, 5 or all of the biomarkers selected from Table 1 can be assayed together.

Another aspect of the invention provides for a method of assessing for suitable dose levels of a Wnt inhibitor, comprising monitoring the differential expression of at least one of the biomarkers after administration of the Wnt inhibitor. For example, after administration of a first bolus of Wnt inhibitor, at least one biomarker is analyzed and based on this result, an increase or decrease in Wnt inhibitor dosage is recommended. After administration of the adjusted dosage of Wnt inhibitor the analysis of at least one biomarker will determine whether the patient is still sensitive to the adjusted dose and that the adjusted dose is providing the expected benefit, e.g., suppressing tumor growth. Alternatively, more than one, for example 2, 3, 4, 5 or all of the biomarkers selected from Table 1 can be assayed together for assessing sensitivity to the dose of the Wnt inhibitor.

In alternative to all embodiments for assessing extended efficacy of a Wnt inhibitor in initially sensitive tumor, the differential expression of NKD1, LEF1 and/or Axin2 can be compared to the expression in a sensitive tumor sample. Sensitive tumor sample is also defined as a tumor that shows more than 50% Axin2 reduction (Wnt pathway inhibition) with the treatment of 50 nM of compound A over 48 hours.

Kits for assessing the activity of any Wnt inhibitor can be made. For example, a kit comprising nucleic acid primers for PCR or for microarray hybridization for the biomarkers selected from Table 1 can be used for assessing sensitivity to a Wnt inhibitor. Alternatively, a kit supplied with antibodies for at least one of the biomarkers would be useful in assaying sensitivity to a Wnt inhibitor.

It is well known in the art that cancers can become resistant to chemotherapeutic treatment, especially when that treatment is prolonged. Assaying for differential expression of at least one of the biomarkers selected from Table 1 can be done after prolonged treatment with any chemotherapeutic to determine if the cancer is sensitive to the Wnt inhibitor. If the patient has been previously treated with another chemotherapeutic or another Wnt inhibitor, it is useful information for the patient to assay for at least one of the biomarkers selected from Table 1 to determine if the tumor is sensitive to a Wnt inhibitor. This assay can be especially beneficial to the patient if the cancer goes into remission and then re-grows or has metastasized to a different site.

Screening for Wnt Inhibitors

It is possible to assay for at least one biomarker selected from Table 1 to screen for other Wnt inhibitor. This method comprises assaying a cell with at least one biomarker, which predicts if the cell is sensitive to a Wnt candidate inhibitor, the cell is then contacted with the candidate Wnt inhibitor and the IC50 of the treated cell is compared with a known Wnt inhibitor contacting a sensitive cell. For example, for cells predicted to be sensitive to any Wnt inhibitor as determined by the differential expression of at least one biomarker, the candidate Wnt inhibitor will have an IC50≤3 µM. The measurement of at least one biomarker expression can be done by methods described previously, for example, PCR or microarray analysis. Alternatively, the combination of more than one the biomarkers can be assayed for this purposes.

TABLE 1

| Gene Name (compound) | Accession number | SEQ ID NO. (nucleotide/protein) |
|---|---|---|
| Notch1 | NM_017617.3/NP_060087/GI: 148833508 | 4851/P46531 |
| Notch2 | NM_024408.3/NP_077719/GI: 24041035 | 4853/Q04721 |
| Notch3 | NM_000435.2/NP_000426/GI: 134244285 | 4854/Q9UM47 |
| AXIN2 | NM_004655.3/NP_004646/GI: 195927059 | 8313/Q9Y2T1 |
| LEF1 | NM_016269/NP_001124185/GI: 7705917 | 51176/Q9UJU2 |
| NKD1 | NM_033119/NP_149110/GI: 14916433 | 85407/Q969G9 |
| SFRP2 | NM_003013.2/NP_003004/GI: 48475052 | 6423/Q96HF1 |
| FRZB | NM_001463.3/NP_001454/GI: 38455388 | 2487/Q92765 |

TABLE 1-continued

| Gene Name (compound) | Accession number | SEQ ID NO. (nucleotide/protein) |
|---|---|---|
| SFRP4 | NM_003014.3/NP_003005/GI: 170784838 | 6424/Q6FHJ7 |
| DKK2 | NM_014421.2/NP_055236/GI: 7657023 | 27123/Q9UBU2 |
| FAM58A | NM_152274.3/NP_689487/GI: 196049382 | 92002/Q8N1B3 |
| FLJ43860 | NM_207414.2/NP_997297/GI: 148727311 | 389690/Q6ZUA9 |
| OR7G3 | NM_001001958.1/NP_001001958/GI: 50080201 | 390883/Q8NG95 |
| CCDC168 | NM_001146197.1/NP_001139669.1/GI: 226246553 | 643677/Q8NDH2 |
| ZNF527 | NM_032453.1/NP_115829/GI: 149192840 | 84503/Q8NB42 |
| CDKN2A | NM_000077.4/NP_478104/GI: 4502749 | 1029/P42771 |
| OR7G3 | NM_001001958.1/NP_001001958/GI: 50080201 | 390883/Q8NG95 |
| WNT11 | NM_004626.2/NP_004617/GI: 17017974 | 7481/O96014 |
| WNT10A | NM_025216.2/NP_079492/GI: 16936520 | 80326/Q9GZT5 |
| WNT3 | NM_030753.3/NP_110380/GI: 13540477 | 7473/P56703 |
| WNT7A | NM_004625.3/NP_004616/GI: 17505191 | 7476/O00755 |
| DTX3L | NM_138287.3/NP_612144.1/GI: 19923717 | 151636/Q8TDB6 |
| HRAS | NM_005343.2/NM_176795.3 NM_001130442.1/NP_001123914.1/GI: 47117697/GI: 194363760/ GI: 194363761 | 3265/P01112 |
| FAT1 | NM_005245.3/NP_005236/GI: 75813622 | 2195/Q14517 |

EXAMPLES

Example 1

Compound A and Compound B (FIGS. 1A and 1B, Respectively) are Potent PORCN Inhibitors in Biochemical and Cellular Assays Radioligand binding assay: Membrane Preparation: Approximately $10^8$ 293 cells were transfected with pcDNA 3.1 constructs (Invitrogen) bearing human PORCN using Fugene 6 (Roche). After 48 hours cells were harvested by scraping in PBS, centrifuged at 1,000×g for 10 minutes. The buffer was aspirated. Cell pellets were frozen in dry ice bath, then gently re-suspended in 10 ml of a 50 mM Tris pH 7.5, 250 mM sucrose buffer containing an EDTA-free protease inhibitor cocktail (Sigma). Cells were lysed using polytron (Brinkman). Lysed cells were centrifuged at 1,600×g for 20 minutes at 4° C., and supernatant was transferred and centrifuged at 20,000 rpm in an SS34 rotor for 20 minutes at 4° C. Supernatants were discarded and the pellets were re-suspended in 10% sucrose, 50 mM Tris pH 7.5, 5 mM $MgCl_2$, 1 mM EDTA solution using three 10-second pulses with a Polytron.

Radioligand labeling of COMPOUND B: Compound C, its structure listed below,

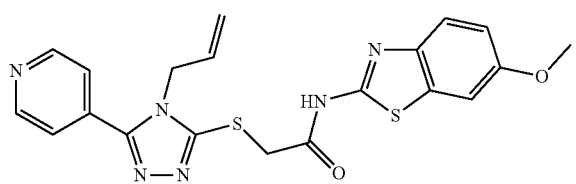 [SMILES: C=CCn1c(SCC(=O)Nc2nc3ccc(OC)cc3s2)nnc1-c1ccncc1]

was radiolabeled through a hydrogenation reaction done by AmBioslabs, to make a $^3H$-radiolabelled COMPOUND B.

Radioligand binding assay: Using the aforementioned membrane preps, filtration binding assays were performed as following. To reduce nonspecific binding, 96-well filtration plates (PerkinElmer) were pre-coated as suggested by the manufacturer with 0.1% BSA and then washed four times with 0.1% BSA. Membrane preps (50 µg total protein) were incubated in polypropylene 96-well plates with 6.6 nM $^3H$-compound B in the presence or absence of COMPOUND A in binding buffer (50 mM Tris pH 7.5, 5 mM $MgCl_2$, 1 mM EDTA, 0.1% bovine serum albumin) plus EDTA-free protease inhibitor cocktail (Sigma) in a final volume of 150 µl for 3 hours at room temperature. Binding reaction mixtures were then transferred to the pre-coated 96-well filtration plates (PerkinElmer), filtered and washed using a 96-pin FilterMate Harvester (PerkinElmer). Radioactive signals were obtained using a Microplate Scintillation Counter, TopCount (PerkinElmer). The radioligand PORCN binding activities were measured by TopCount (PerkinElmer). Curve fitting was performed using Prism.

Figure 2B:
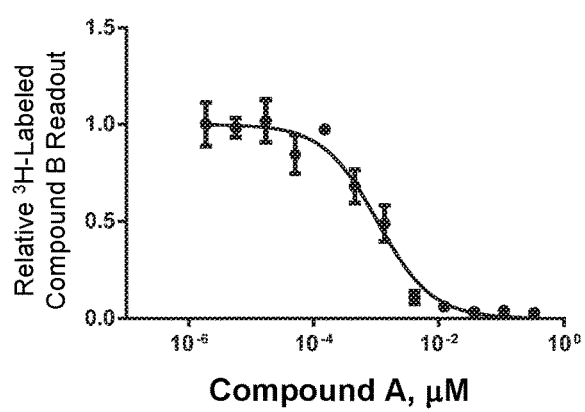
FIG. 2B shows the binding of COMPOUND A to PORCN.

As shown in FIG. 2A, tritium labelled COMPOUND B bound greatly to the membrane preparations from 293 cells transfected with PORCN but not to those from Wntless or vector control transfected cells, showing that COMPOUND B specifically interacted with PORCN. Furthermore, the specific interaction between COMPOUND B and PORCN could be competed off by unlabelled COMPOUND B (FIG. 2A). COMPOUND B bound to PORCN and served as a hot radioligand in the in vitro biochemical PORCN binding assay, for competition with cold testing compounds. In the radioligand binding assay to PORCN using $^3H$-COMPOUND B, COMPOUND A showed an IC50 of 1 nM (FIG. 2B).

Example 2

Inhibition of PORCN by COMPOUND A Blocks In Vitro Wnt Signaling

Reporter gene assay: Mouse Leydig cell TM3 cells (obtained from American Type Culture Collection, ATCC, Manassas, Va.) are cultured in 1:1 mixture of Ham's F12 medium and Dulbecco's modified Eagle's medium (Gibco/Invitrogen, Carlsbad, Calif.) supplemented with 2.5% FBS (Gibco/Invitrogen, Carlsbad, Calif.) and 5% horse serum (Gibco/Invitrogen, Carlsbad, Calif.), 50 unit/mL penicillin and 50 µg/mL of streptomycin (Gibco/Invitrogen, Carlsbad, Calif.) at 37° C. with 5% CO2 in air atmosphere. TM3 cells in a 10 cm dish are co-transfected with 8 µg of STF-reporter plasmid containing a luciferase gene driven by Wnt-responsive elements and 2 µg of pcDNA3.1-Neo (Gibco/Invitrogen, Carlsbad, Calif.) with 30 µL of FuGENE6 (Roche Diagnostics, Indianapolis, Ind.) following the manufacturer's protocol. Stable cell lines (TM3 Wnt-Luc) were selected with 400 µg/mL of G418 (Gibco/Invitrogen, Carlsbad, Calif.). The TM3 Wnt-Luc cells and L-cell Wnt3A cells (obtained from American Type Culture Collection, ATCC, Manassas, Va.) were cultured in Dulbecco's modified Eagle's medium (Gibco/Invitrogen, Carlsbad, Calif.) supplemented with 10% FBS (Gibco/Invitrogen, Carlsbad, Calif.) and 50 unit/mL penicillin and 50 µg/mL of streptomycin (Gibco/Invitrogen, Carlsbad, Calif.) at 37° C. with 5% CO2 in air atmosphere) are trypsinized and co-cultured into a 384-well plate with DMEM medium supplemented with 2% FBS, and treated with different concentrations of a compound of the invention. After 24 hours, the firefly luciferase activities are assayed with the Bright-Glo™ Luciferase Assay System (Promega, Madison, Wis.). The $IC_{50}$ is measured when the effect of the compound reduces the luminescence signal by 50%.

Figure 3A:
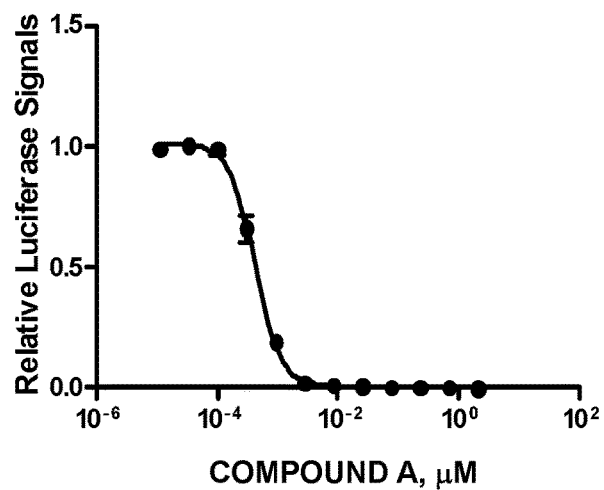
FIG. 3A shows COMPOUND A potent inhibition of Wnt signaling in the Wnt co-culture assay with an IC50 of 0.4 nM.
Figure 3B:
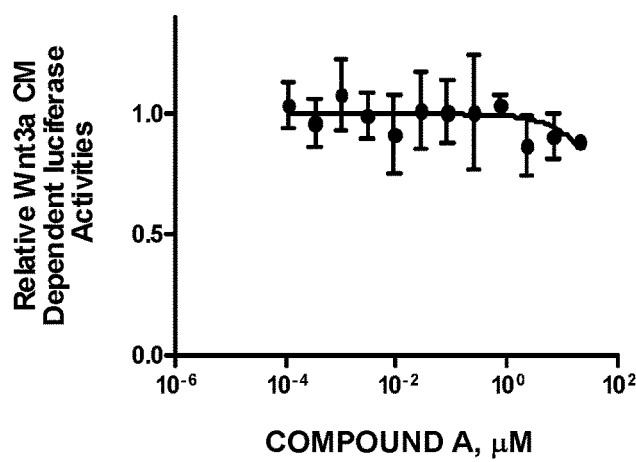
FIG. 3B depicts that the inhibitory effect was rescued by the addition of exogenous Wnt3A conditioned medium.
Figure 4:
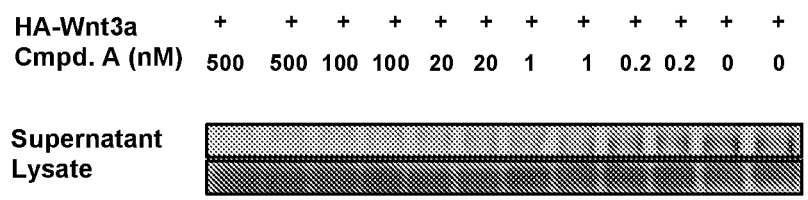
FIG. 4 shows the effect of various doses of COMPOUND A on 293A cells that were transfected with HA-Wnt3A.

COMPOUND A potently inhibited Wnt signaling in the Wnt co-culture assay with an IC50 of 0.4 nM (FIG. 3A). This inhibitory effect was rescued by the addition of exogenous Wnt3A conditioned medium (FIG. 3B). To further confirm its function in PORCN dependent Wnt secretion, 293A cells were transfected with HA-tagged Wnt3a (HA-Wnt3A) and treated with various doses of COMPOUND A. As shown in FIG. 4, COMPOUND A potently attenuated the abundance of HA-Wnt3A in the supernatant while sparing the lysate HA-Wnt3A, suggesting that Wnt3A secretion s substantially inhibited by COMPOUND A in a dose dependent manner. The secreted Wnts subsequently function on Wnt receiving cells that leads to phosphorylation of the Wnt co-reportert LRP6. Using autocrine L-Wnt3A cells, a mouse mammary cell line overexpressing Wnt3A, we demonstrated that COMPOUND A indeed strongly blocked Wnt dependent phosphorylation a LRP6 (low density lipoprotein receptor-related protein 6) (FIG. 5A). PORCN was reported to affect pan-Wnt post-translational palmitoylation[17-18]. The residues around the putative Wnt palmitoylation site, Ser209, are conserved among all 19 Wnts (FIG. 5B), and the CHGxSGSC palmitoylation motif ("SGSC" disclosed as SEQ ID NO: 1) was not identified in any other protein throughout the proteome. To test if COMPOUND A can recapitulate the consequence of loss of PORCN, genetically, we focused on a set of canonical Wnts in the Wnt dependent STF reporter assays, including Wnt1, 2, 3, 3A, 6, 7A, and 9A. As shown in FIG. 5C, COMPOUND A demonstrated comparable inhibitory activities against all tested Wnts, which is consistent with the loss of PORCN phenotype. Additionally, COMPOUNd A showed no major cytotoxicity in cells up to 20 µM.

Example 3

Cellular Functional Effects of a Wnt Inhibitor in Human Head Neck Cancer Cell Lines To identify human cancer cell lines that respond to porcupine inhibition, we profiled over 300 cell lines using the mRNA expression level of AXIN2 as readout. All cell lines were cultured in a humidified incubator at 37° C. with 5% CO2. HN30 cells (Wayne State University) and UMSCC cells (University of Michigan) are derived from human head neck squamous cell carcinoma (HNSCC) patient tumor samples. Total RNA or DNA was isolated using the Qiagen RNeasy and DNeasy blood and tissue kit, according to the manufacturer's instruction, respectively. Briefly, cells were disrupted by adding Buffer RLT and homogenized using QlAshredder spin columns. After one volume of 70% ethanol was added to the homogenized lysate and thoroughly mixed, the samples were transferred to RNeasy spin column. The flow-through was discarded after centrifuge. After washing the RNeasy spin columns with Buffer RW1 and Buffer RPE twice, RNA samples were collected by eluting the RNeasy spin columns with RNase-free water. For TaqMan assay, $2×10^6$ cells per well were plated into 6-well cell culture plates and treated with or without compound in a multi-point dose-response starting from 5 µM as the highest final concentration. 48 hours later, RNA samples were collected.

Figure 6:
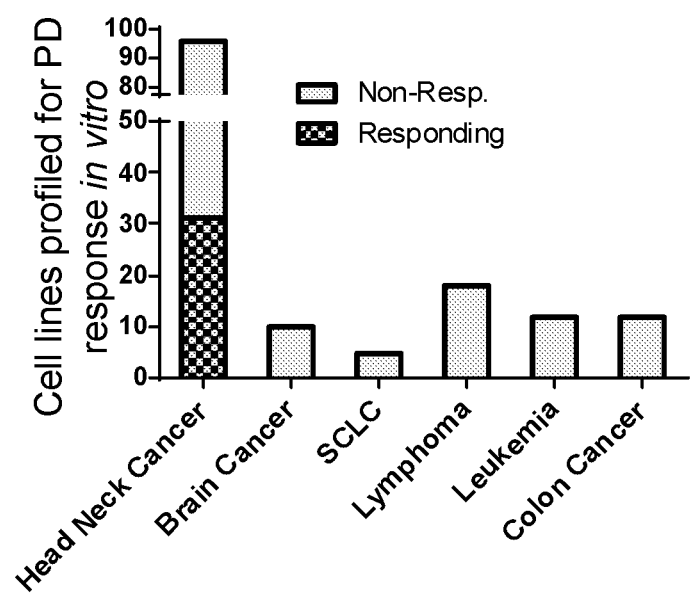
FIG. 6. A response of various cell lines per cancer type to the treatment with COMPOUND A. A responsive cell line is defined as achieving greater than 50% AXIN2 mRNA reduction after the treatment with 10-100 nM of COMPOUND A for 48 hours.

A responsive cell line is defined as achieving greater than 50% AXIN2 mRNA reduction after the treatment with 10-100 nM of COMPOUND A for 48 hours, preferably after the treatment with 50 nM of COMPOUND A for 48 hours. As shown in FIG. 6, head and neck cancer cell (HNSCC) lines are among the top cancer types that were responsive to COMPOUND A. Among the HNSCC cell lines, 31 out of 96 showed pathway inhibition upon the treatment of COMPOUND A (FIG. 7).

In order to correlate the pathway inhibition with cellular function, the human HNSCC cell line HN30 was used for further in vitro and in vivo characterization. For colony formation assay, $2×10^3$ cells per well were plated into 6-well cell culture plates with or without compound treatment. Cells were stained with crystal violet one week later.

COMPOUND A potently inhibited Wnt-dependent AXIN2 message production in HN30 with an IC50 of 0.3 nM (FIG. 8A). It strongly attenuated HN30 colony formation albeit with a right-shifted IC50 (FIG. 8B). The reduced colony formation effect by COMPOUND A could be partially rescued with overexpression of dominant β-catenin (FIG. 9A). To further confirm whether the cellular effect of COMPOUND A was due to the inhibition of PORCN-dependent Wnt signaling activities, shRNA experiments were performed. shRNA against PORCN substantially inhibited the expression of the Wnt target gene AXIN2 (FIG. 9B) and the colony formation of HN30 cells in vitro (FIG. 9C), consistent with the COMPOUND A data.

Example 4

Efficacy of a Wnt Inhibitor in a Mouse Model of Wnt-dependent Human HNSCC

To test the anti-tumor activity of COMPOUND A, a mouse xenograft model of HNSCC HN30 was established. Nude mice bearing HN30 tumors were randomized according to tumor volume. COMPOUND A was formulated in 10% citrate buffer pH 2.8/90% citrate buffer pH 3.0, or 0.5% MC/0.5% Tween 80 and administered by oral gavage at a dosing volume of 10 µL/g of an animal body weight. Body weight was monitored daily and tumor sizes were assessed three times a week once tumors were palpable. Tumor sizes were determined by using caliper measurements. Tumor volumes were calculated with a formula (Length×Width×Height)/2. The plasma concentrations and exposures of COMPOUND A in the tumor bearing nude mice (n=2 per dosing group) were determined on day 14. Blood sample (50 µL) was collected by serial retroorbital sampling at 1, 3, 7, 16 and 24 hours post-dose. The blood samples were centrifuged and plasma separated and frozen until analysis by LC/MS/MS.

As shown in FIG. 10A, COMPOUND A induced dose-dependent efficacy when dosed once a day. Changes in tumor weight for each treated (T) and control (C) groups were measured and used to calculate growth delay as expressed by the T/C ratio. After 14 days of treatment, a dose of 0.1 mg/kg led to moderate tumor growth delay (T/C: 69%), and a dose of 0.3 mg/kg significantly inhibited the tumor growth (T/C: 26%), and doses of 1.0 and 3.0 mg/kg resulted in substantial tumor regression (T/C: −31% and −50% respectively) (FIG. 10A). The regimen was well tolerated and there was no significant animal body weight loss. A similar result was obtained when dosed twice a day in this model with −44% T/C at a dose of 0.5 mg/kg twice a day.

AXIN2 mRNA and pLRP6 levels (determined as in Example 3) were utilized as pharmacodynamic markers to link the observed anti-tumor activity in the HN30 mouse xenograft model. After a single dose of COMPOUND A at 3 mg/kg, the levels of AXIN2 mRNA expression in tumors were reduced by ~60-95% between 5 and 10 hours post dose and the effect started to diminish at 16 hours along with decreasing drug concentrations (FIG. 10B). A time delay was observed between the peak drug concentration (at 1 hour) and the maximum AXIN2 mRNA inhibition (at 10 hours). Additionally, as shown in FIG. 10C, pLRP6 levels in the HN30 tumors were substantially reduced in a time dependent manner. The maximum effect was achieved at 7-10 hours post dose and the pLRP6 levels were largely back to normal by 24 hours. The treatment with the COMPOUND A caused also 84% downregulation for LEF1 and 67% downregulation for NKD1. This pharmacokinetic (PK), PD, and efficacy relationship explains that the sustained pathway inhibition is not required for inducing tumor regression in this HN30 xenograft model, which may provide a key differentiation factor between tumors and normal tissues to achieve a therapeutic window. It can be concluded that a Wnt inhibitor, particularly a compound A can be used in the treatment of head and neck cancer.

Example 5

Prediction of Wnt Inhibitor Sensitivity in Human Primary Tumor Mouse Xenograft Model and in Human Primary Tumors by Assessing the Gene Expression of Notch1, Notch2, Notch3, LEF1, NKD1, SFRP2, FRZB, SFRP4 and DKK2

To examine other Wnt related genes regulated by the treatment of COMPOUND A in vivo, a TaqMan® GeneCard analysis revealed down-regulation of several other known Wnt target genes including LEF1 and NKD1, as well as Wnt ligands including Wnt3 and Wnt9B.

For this a two-Step TaqMan RT-PCR analysis was performed on a PTC-200 peltier thermal cycler (MJ Research) and an ABI PRISM 7900HT Sequence Detection system (Applied Biosystems). Firstly, cDNA was synthesized using a High-Capacity cDNA Archive kit (Applied Biosystems) according to the manufacturer's instructions. Briefly, the RT reaction was prepared by mixing non-enzymatic, enzymatic components of the High-Capacity cDNA Archive kit and isolated RNA samples, followed with tandem incubation at 25° C. for 10 min and 37° C. for 120 min using a thermal cycler. Secondly, TaqMan analyses were performed using TaqMan Universal Master mix (Applied Biosystems) and AXIN2 and GAPDH probes (Applied Biosystems) according to the manufacturer's instructions. Briefly, the PCR reaction was prepared by mixing Universal Master mix, TaqMan probes and synthesized cDNA samples. The PCR cycle is as following: 95° C. for 10 min and 40 cycles of tandem incubation at 95° C. for 15 sec and 60° C. for 1 min. mRNA expression levels for the target genes were normalized to GAPDH mRNA levels and data were analyzed using SDS 2.0 software (Applied Biosystems) to calculate relative RNA quantities. Curve fitting was performed using Prism.

For GeneCard analysis, 96-well TaqMan array gene card was used according to the manufacturer's instruction. The gene card assays were run on ABI 7900HT Real-Time PCR System (Applied Biosystems) and analyzed with the ΔΔCt method.

When comparing the gene expression patterns between HN30 tumors and normal human oropharynx tissues using the GeneCard analysis, Wnt ligands including Wnt3, 7A, 10A and 11 were substantially overexpressed in HN30 tumors whereas the known Wnt inhibitory genes such as SFRP2, FRZB, SFRP4 and DKK2 were substantially downregulated, which is consistent with the hypothesis that Wnt signaling is an etiological target. This data indicates it is more likely for a cell line, cancer sample or a patient having a cancer type to be sensitive to a Wnt inhibitor if the SFRP2, FRZB, SFRP4 or DKK2 gene expression is found to be differentially downregulated compared to a control. Cancer sample or a cancer having the SFRP2, FRZB, SFRP4 or DKK2 gene expression differentially downregulated compared to a control are more likely to be sensitive to a Wnt inhibitor compared to a cancer sample or a cancer exhibiting comparable gene expression to a control. This notion can be applied in a patient stratification process, where patients that would most likely respond to the treatment with a Wnt inhibitor are selected and treated.

In order to further understand the mechanism of action in the cells that responded to COMPOUND A treatment, including HN30 cells, exome sequencing was performed on 40 HNSCC cell lines, with 25 responsive lines and 15 non-responsive lines. TP53, CDKN2A, Notch1/2/3, PTEN, HRAS and PIK3CA were among the top oncogenes or tumor suppressor genes mutated in this set of cell lines (FIG. 11).

Whole exome capture library preparation and sequencing: Exome Capture Library Construction was done using the Roche NimbleGen V2 (44.1 Mbp) exome enrichment kit (Otogenetics). Paired-end sequencing (2×100 bp) of the captured exons was carried out on an Illumina Genome Analyzer IIx platform with an average coverage of 50× (Otogenetics).

Sequence data processing: Sequencing data were processed by a standard pipeline recommended by Broad Institute Genome Atlas Tool Kit (GATK):

The raw sequencing fastq files with reads and quality scores for each sample were aligned to the NCBI human reference genome GRCh37 using Burrows-Wheeler Aligner version 0.5.9(http://bio-bwa.sourceforge.net). For each sample, a single sorted Binary Alignment Map (BAM) file with their alignments to the reference genome was generated.

The BAM files from the alignment were further cleaned using "sample level realignment with known indels and recalibration" method. (http://www.broadinstitute.org/gatk/guide)

The GATK unified genotyper was used for each recalibrated and cleaned BAM file to generate SNP, Multiple Nucleotide Polymorphism (MNP), and indel. After variant calls for each sample, they were merged into multi-sample SNP and indel calling. Separated Variant Call Format (VCF) files were produced for SNP and indel calling.

All variants calls were then processed by SnpEff (v2.1b http://snpeff.sourceforge.net/) to predict their functional impacts on corresponding protein products, and by GATK's variant annotator for additional annotations. Various publically available databases including dbSNP v.135, COSMIC v.58, and ESP5400 were used to map the genomic changes to known variants.

Analysis of variants: To reduce the sequencing artifact, various filtrations were employed, including variant quality <30, mapping quality <30, variant confidence <2, and normalized Phred-scaled likelihoods >80. There are a total of 18349 genes harboring genomic changes compared to the reference exome. The total number of genomic changes in all 40 HNSCC cell lines is about 169 k. However, most of them (89%) are known variants annotated in the public databases mentioned above. Among the novel variants, about half (6% of total) of variants result in protein sequence modification, such as mutations, truncations, insertions, and deletions. Note that all the sequencing was for cell lines where no matched normal was available. Therefore, some of the novel variants seen here potentially could be SNPs. Mutations acquired during cell line passage are also possible and cannot be distinguished from those acquired during cancer development and progression. The UM-SCC lines each have unique genotypes and were used at the lowest possible passage number usually less than 100 passages from initial culture.

The functional impacts of genomic changes were assessed by SnpEff. The high impact mutations include frame shift, splice site mutations, start codon loss, stop codon gain, and stop codon loss. The moderate impact mutations include in-frame insertion or deletion and nonsynonymous mutations. The potential germline mutation was determined by whether the mutation is annotated in dbSNP with SNP allele origin (SAO) <2 or in an ESP5400 entry and not in COSMIC.

To study the correlation between loss of function mutations and COMPOUND A pharmacological function, we aggregated all likely loss of function (LoF) variants into one category as it is known that LoF mutations of a gene may have mutations spreading across a wide range of the protein sequence. Mutations included high impact variants such as stop codon gain, frame shift, start codon loss, and splice site mutations. We also required combined sequence depth for wild type and mutant allele to be at least 5, to remove extremely low coverage variants. Using the variant calls from 40 HNSCC cell lines that were sequenced, We evaluated the enrichment effect of LoF variants on COMPOUND A PD response for each gene. The enrichment factor is defined as the following (i.e. odds ratio), $$E(\text{LoF}) = (P(\text{responding}|\text{mutant})[1-P(\text{responding})]) / (P(\text{responding})[1-P(\text{responding}|\text{mutant})])$$

Where P(responding|mutant) represents the probability of responding to COMPOUND A treatment given the gene harboring a LoF mutation, and P(responding) represents the probability of responding to COMPOUND A treatment by chance.

Example 6

Notch1 is the Most Predictive Biomarker for the Treatment with a Wnt Inhibitor

The candidate genes were selected based on E>2 and the number of LoF occurrence larger than 3. Among the top candidates, Notch1 LoF has one of the highest enrichment factors, 3 fold enrichment over random selection. Notch1 mutations/variants were validated by sequencing of cDNA or genomic DNA of the cancer cell lines (GeneWiz). Sequences were analyzed using Sequencher (GeneCodes).

From this data we can conclude that one of the most striking features correlating the gene mutation status and cell line pathway inhibition responses to COMPOUND A was the Notch1 loss of function (LoF) mutation in the responsive cell lines.

As shown in FIGS. 13A and 13B, five frameshift/nonsense mutations have been identified among the responsive cell lines, with only one Notch1 nonsense mutation among the non-responsive cell lines. Interestingly, all cells with Notch1 mutations harbored at least one mutant allele that affected the N-terminus of Notch1. This is consistent with the notion that the N-terminus of Notch1 is required for its function, with the N-terminal EGF repeats responsible for ligand-receptor interaction[17], such that mutations in this region are more likely to be LoF mutations. To further characterize the functional consequence of the missense mutations, such as Notch1 C478F, identified in the HN30 cells, a Notch reporter gene assay was performed with overexpression of the wild type or the C478F mutant (FIG. 13C). The C478F mutation is located in the extracellular domain of Notch1, which is presumably critical for Notch receptor and ligand interaction. Indeed, in the presence of the Notch ligand DLL1, the activity of mutant C478F Notch1 was abolished in this Notch reporter gene assay (FIG. 13C).

This may all provide guidance to patient selection in support of the clinical treatment of PORCN inhibitors such as for example COMPOUND A.

DTX3L (Deltex 3-like, also called BBAP, B-lymphoma- and BAL-associated protein) heterozygous nonsense mutation was identified in the HNSCC cell line SNU1076. DTX3L is an E3 ubiquitin ligase. Its cellular function in the mammalian Notch pathway is not clear, but its *Drosophila* homologue Deltex is a positive regulator of Notch signaling in *Drosophila*. In a SNU1076 xenograft model in mice, COMPOUND A at the dose of 5 mg/kg significantly inhibited the tumor growth (T/C: 25%) after 14 days of treatment (FIG. 14A). Moreover, COMPOUND A substantially inhibited the Wnt pathway, as indicated by 70% reduction of AXIN2 (FIG. 14B). Loss of DTX3L may provide an alternative mechanism to inactivate the Notch signaling pathway with subsequent activation of Wnt signaling.

Example 7

HRAS and FAT1 as Predictive Maker for the Treatment with a Wnt Inhibitor

From our exome sequencing and cell line profiling efforts, we observed an enrichment of compound A responders in FAT1 mutant head and neck cancer cell lines (FIG. 15). Furthermore, from our analysis, 4 of 5 cell lines harbouring HRAS mutations responded to compound A (FIG. 16).

Example 8

Prediction of Cell Line Chemical Sensitivity to Wnt Inhibitor from Genomic Data and Clinical Implication As determined by exome sequencing Notch1 gene expression (e.g. mutation status) is one of the most powerful indicators of Wnt inhibitor sensitivity, and therefore can be used as the stratification biomarker to be considered for selecting cancer patients responsive to an Wnt inhibitor, such as for example COMPOUND A. The association of Notch1 LoF mutation to chemical sensitivity of Wnt inhibitor in a panel of cancer-relevant cell lines showed that Notch1 is valuable in predicting patient sensitivity to a Wnt inhibitor. Notch1 LoF mutation is for prediction of pathway inhibition response based on bioinformatics analysis of 40 head neck cancer cell lines (as described above). In addition to Notch1 and based on tumor model, SFRP2, FRZB, SFRP4 and DKK2 correlated also with efficacy of a Wnt inhibitor. Even better predictive power is expected when a set of at least two biomarkers from the ones described herein, are used to predict the sensitivity. With the help of bioinformatics, further set of useful biomarkers that can be used for patient stratification was identified—FAM58A, FLJ43860, NOTCH1, CDKN2A, OR7G3, CCDC168, ZNF527, HRAS and FAT1. As the incidence of Notch1 LoF mutation is relatively high in HNSCC patients, Notch1 gene expression is particularly suitable to select HNSCC patients. The association of NOTCH1 LoF mutation to chemical sensitivity of Wnt inhibitors in a panel of cancer cell lines showed that NOTCH1 has a predictive value of 3 fold enrichment over random selection. Other aforementioned biomarkers also are associated with preclinical models that were sensitive to a Wnt inhibitor. As an extrapolation to the clinical setting, patient selection based on the aforementioned biomarkers would increase the likelihood of clinical response upon treatment with a Wnt inhibitor.

REFERENCE

1 Polakis, P. Wnt signaling in cancer. Cold Spring Harbor perspectives in biology 4, doi:10.1101/cshperspect.a008052 (2012).
2 Nusse, R. & Varmus, H. Three decades of Wnts: a personal perspective on how a scientific field developed. The EMBO journal 31, 2670-2684, doi:10.1038/emboj.2012.146 (2012).
3 Clevers, H. & Nusse, R. Wnt/beta-catenin signaling and disease. Cell 149, 1192-1205, doi:10.1016/j.cell.2012.05.012 (2012).
4 Seshagiri, S. et al. Recurrent R-spondin fusions in colon cancer. Nature 488, 660-664, doi:10.1038/nature11282 (2012).
5 Hao, H. X. et al. ZNRF3 promotes Wnt receptor turnover in an R-spondin-sensitive manner. Nature 485, 195-200, doi:10.1038/nature11019 (2012).
6 Koo, B. K. et al. Tumour suppressor RNF43 is a stem-cell E3 ligase that induces endocytosis of Wnt receptors. Nature 488, 665-669, doi:10.1038/nature11308 (2012).
7 Grigoryan, T., Wend, P., Klaus, A. & Birchmeier, W. Deciphering the function of canonical Wnt signals in development and disease: conditional loss- and gain-of-function mutations of beta-catenin in mice. Genes & development 22, 2308-2341, doi:10.1101/gad.1686208 (2008).
8 Aoki, K. & Taketo, M. M. Tissue-specific transgenic, conditional knockout and knock-in mice of genes in the canonical Wnt signaling pathway. Methods Mol Biol 468, 307-331, doi:10.1007/978-1-59745-249-6_24 (2008).
9 Wang, Y. Wnt/Planar cell polarity signaling: a new paradigm for cancer therapy. Molecular cancer therapeutics 8, 2103-2109, doi:10.1158/1535-7163.MCT-09-0282 (2009).
10 Herr, P., Hausmann, G. & Basler, K. WNT secretion and signalling in human disease. Trends in molecular medicine 18, 483-493, doi:10.1016/j.molmed.2012.06.008 (2012).
11 Takada, R. et al. Monounsaturated fatty acid modification of Wnt protein: its role in Wnt secretion. Developmental cell 11, 791-801, doi:10.1016/j.devcel.2006.10.003 (2006).
12 Biechele, S., Cox, B. J. & Rossant, J. Porcupine homolog is required for canonical Wnt signaling and gastrulation in mouse embryos. Developmental biology 355, 275-285, doi:10.1016/j.ydbio.2011.04.029 (2011).
13 Barrott, J. J., Cash, G. M., Smith, A. P., Barrow, J. R. & Murtaugh, L. C. Deletion of mouse Porcn blocks Wnt ligand secretion and reveals an ectodermal etiology of human focal dermal hypoplasia/Goltz syndrome. Proceedings of the National Academy of Sciences of the United States of America 108, 12752-12757, doi:10.1073/pnas.1006437108 (2011).
14 Wang, X. et al. Mutations in X-linked PORCN, a putative regulator of Wnt signaling, cause focal dermal hypoplasia. Nature genetics 39, 836-838, doi:10.1038/ng2057 (2007).
15 Grzeschik, K. H. et al. Deficiency of PORCN, a regulator of Wnt signaling, is associated with focal dermal hypoplasia. Nature genetics 39, 833-835, doi:10.1038/ng2052 (2007).
16 Leemans, C., Braakhuis, B., Brakenhoff, R., The molecular biology of head and neck cancer. Nat Rev Cancer. 11 (1), 9-22, doi: 10.1038/nrc.2010.12.16 (2011)
17 Kopan R (2012) Notch signaling. Cold Spring Harbor perspectives in biology 4(10).

The invention claimed is:

1. A method of predicting the sensitivity of a cancer cell in a sample by using a Wnt inhibitor named 2-[5-methyl-6-(2-methylpyridin-4-yl)pyridin-3-yl]-N-[5-(pyrazin-2-yl)pyridin-2-yl]acetamide, or a pharmaceutically acceptable salt thereof, the method comprising:
   a) contacting a cancer cell with the Wnt inhibitor named 2-[5-methyl-6-(2-methylpyridin-4-yl)pyridine-3-yl]-N-[5-(pyrazin-2-yl)pyridin-2-yl]acetamide, or a pharmaceutically acceptable salt thereof;
   b) measuring gene expression of at least one biomarker which is Notch-1 in the cell;
   c) comparing the gene expression of the at least one biomarker with gene expression from a normal or control cell;
   d) predicting the sensitivity of the cancer cell to the Wnt inhibitor from the comparison of the differential gene expression based on reduced expression of the at least one biomarker in the cancer cell when compared to the normal or control cell;
   and wherein the IC50 of the cancer cell contacted with the Wnt inhibitor is less than 1 µM.

2. Method according to claim 1, wherein the differential gene expression of the at least one biomarker indicates a functional Wnt pathway.

3. Method according to claim 1, wherein the cancer is a head and neck squamous cell carcinoma.

4. Method according to claim 1, further comprising measuring gene expression of AXIN2, LEF1 and/or NKD1 in the cell contacted with the WNT inhibitor; comparing the gene expression of AXIN2, LEF1 and/or NKD1 with an untreated or placebo treated control cell; and correlating a reduced differential expression of Axin2, LEF1 and/or NKD1 when compared with the expression of Axin2, LEF1 and/or NKD1 from the untreated or placebo treated control cell to the sensitivity of the cancer cell to a Wnt inhibitor.

5. Method according to claim 1, wherein the IC50 of the cancer cell contacted with the Wnt inhibitor is less 0.5 µM.

6. Method according to claim 5, wherein the IC50 of the cancer cell contacted with the Wnt inhibitor is less than 0.2 µM.

* * * * *